(12) United States Patent
Walker et al.

(10) Patent No.: US 8,319,637 B2
(45) Date of Patent: Nov. 27, 2012

(54) METHODS AND APPARATUS FOR FACILITATING TESTING OF THE SOBRIETY OF ONLINE GAMBLERS

(75) Inventors: Jay S. Walker, Ridgefield, CT (US); Zachary T. Smith, Norwalk, CT (US); Magdalena M. Fincham, Ridgefield, CT (US)

(73) Assignee: IGT, Reno, NV (US)

( * ) Notice: Subject to any disclaimer, the term of this patent is extended or adjusted under 35 U.S.C. 154(b) by 233 days.

(21) Appl. No.: 12/823,106

(22) Filed: Jun. 24, 2010

(65) Prior Publication Data

US 2010/0328066 A1 Dec. 30, 2010

Related U.S. Application Data

(60) Provisional application No. 61/220,197, filed on Jun. 24, 2009.

(51) Int. Cl.
*G08B 21/00* (2006.01)

(52) U.S. Cl. ............... 340/540; 340/539.11; 340/323 R; 340/5.33; 463/16; 463/17; 463/21; 704/251

(58) Field of Classification Search .................. 340/540, 340/539.11, 323 R, 825.22, 5.33, 5.61; 463/12, 463/16, 17, 21; 704/249, 251; 706/11, 12
See application file for complete search history.

(56) References Cited

U.S. PATENT DOCUMENTS

| 6,561,811 B2 * | 5/2003 | Rapoza et al. ................ 434/236 |
| 2009/0037351 A1 * | 2/2009 | Kristal et al. .................... 706/12 |
| 2009/0143661 A1 * | 6/2009 | Taub et al. ..................... 600/365 |

* cited by examiner

*Primary Examiner* — Hung T. Nguyen
(74) *Attorney, Agent, or Firm* — Magdalena M. Fincham; Fincham Downs, LLC

(57) ABSTRACT

Methods, systems and articles of manufacture are provided for administering sobriety tests to online gamblers, as well as to determining whether, when and to whom to administer a sobriety tests. Various mediation events to be initiated upon certain results of such sobriety tests are also disclosed.

26 Claims, 10 Drawing Sheets

300

| PLAYER NAME: JOHN SMITH | 305 |
| --- | --- |
| PLAYER IDENTIFIER: JOHN_SMITH_0035 | 310 |
| NORMAL SOBRIETY SCORE: 19/20 | 315 |
| PLAYER STATUS: B | 320 |
| SESSION IDENTIFIER: S13471920 | 325 |
| SESSION TIME: 1/20/2010 10:43 TO 1/20/2010 12:51 | 330 |

| TESTING TIME 335 | SOBRIETY SCORE 340 |
| --- | --- |
| 10:43 | 19/20 |
| 11:43 | 20/20 |
| 12:43 | 18/20 |

| SESSION IDENTIFIER: S37192218 | 345 |
| --- | --- |
| SESSION TIME: 2/11/2010 3:45 TO 2/11/2010 6:21 | 350 |

| TESTING TIME 355 | SOBRIETY SCORE 360 |
| --- | --- |
| 3:45 | 18/20 |
| 4:45 | 15/20 |

FIG. 3

METHODS AND APPARATUS FOR FACILITATING TESTING OF THE SOBRIETY OF ONLINE GAMBLERS

CROSS REFERENCE TO RELATED APPLICATIONS

This application claims the benefit of U.S. Provisional Application Ser. No. 61/220,197, filed on Jun. 24, 2009 in the name of Walker et al. The entirety of this Application is incorporated by reference herein for all purposes.

BRIEF DESCRIPTION OF THE FIGURES

FIG. 3 is a table representative of one embodiment of an online gambler database according to one or more embodiments described herein.

DETAILED DESCRIPTION

A. Introduction

Figure 1A:
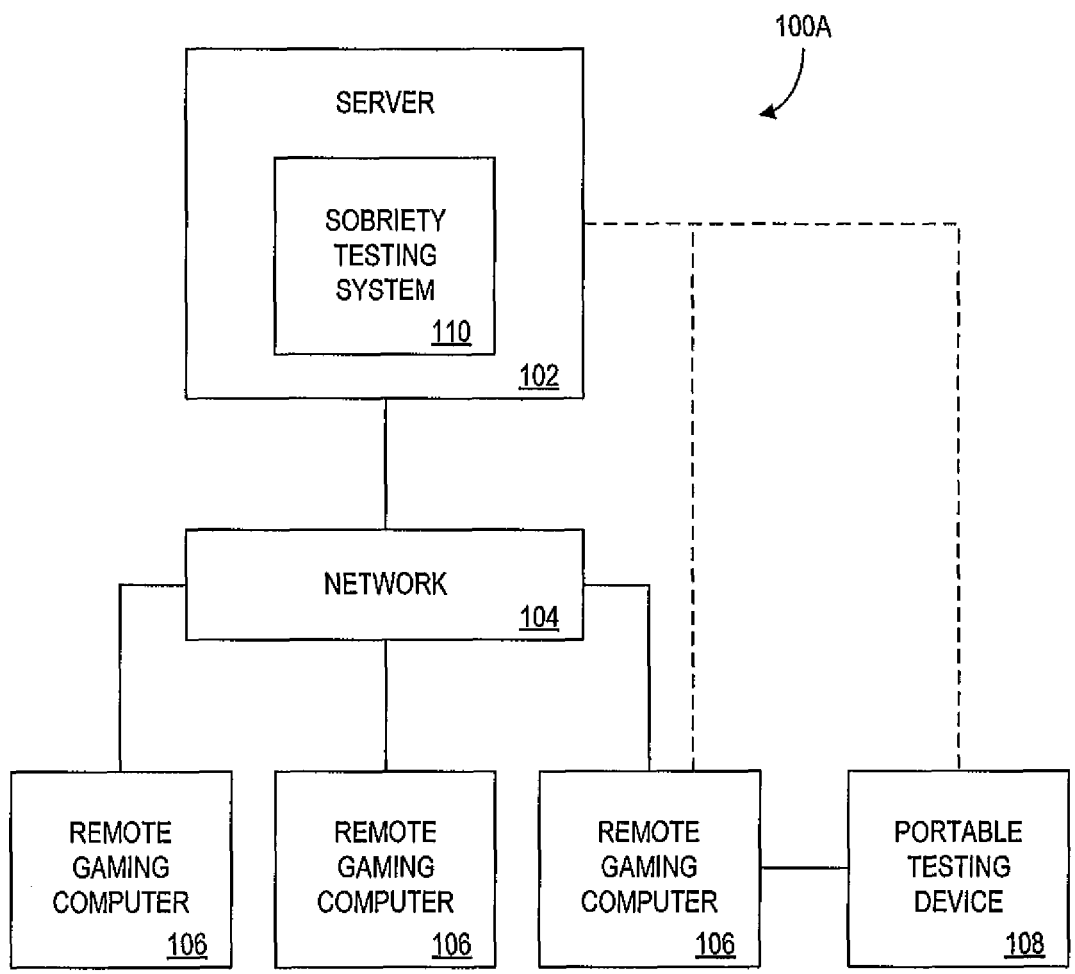
FIG. 1A is a schematic diagram of an embodiment of a system in accordance with one or more embodiments described herein.

Applicants have recognized that in the event online gambling becomes legalized in some jurisdictions and thus significant amounts of wagering takes place online, it may prove beneficial to provide for mechanisms that identify whether an online gambler is intoxicated or has his judgment unacceptably impaired such that his gambling activities should either be suspended or modified in a manner that minimizes harm resulting from his intoxication or otherwise impaired judgment (e.g., such harm consisting of excessive gambling that the gambler would not have participated in had his judgment not been so impaired).

Accordingly, consistent with one or more embodiments, apparatus, systems, articles of manufacture and methods described herein provide for helping certain entities (e.g., online casinos, regulators, law enforcement personnel and/or online gamblers themselves) determine whether a player is intoxicated (or has his or her judgment otherwise unacceptably impaired). For example, a sobriety test may be administered to the player to determine whether the player is intoxicated. A wide variety of example sobriety tests, as well as example mechanisms for administering such and determining whether, when and to whom to administer such tests, are described herein.

In accordance with some embodiments, apparatus, systems, articles of manufacture and methods described herein provide for determining, facilitating and/or administering certain mediation measures if it is determined that an online gambler (also referred to as a player herein) is intoxicated (e.g., if the player does not pass a sobriety test and/or the results of such a test indicate a cause for concern with respect to the player's intoxication). Examples of such mediation measures include, but are not limited to: (i) pausing or interrupting an online gambling session of the player, (ii) preventing the player from gambling further (e.g., for some predetermined period of time or until the player passes a sobriety test), (iii) outputting a message to the player (e.g., informing the player of the results of the sobriety test or requesting that the player modify his gambling activity), (iv) outputting a message to another entity (e.g., a spouse or other person associated with the player, a casino employee, a third party service for facilitating such mediation, a regulatory body), (v) modifying one or more parameters of game play for the player (e.g., decreasing the magnitude of the highest acceptable wager amount, slowing the rate at which the player may place consecutive wagers, restricting access to one or more games, turning on/off game features (such as such as distracting sounds, extra bets, bonus rounds, story mode), changing the game's display). Changing features of the game's display may include highlighting balance in some manner, tracking and presenting data that is not normally displayed (e.g., amount lost, time played, loss to time ratio,) eliminating distractions such as the animations on a slot reel (i.e., make the game duller).

In accordance with some embodiments described herein, online gamblers may be asked to complete sobriety tests before and/or during a session of gambling. In some embodiments, such sobriety tests may need to be initiated and/or completed before the player is allowed to start and/or continue gambling (in some embodiments, before the player is allowed to start and/or continue gambling for real money or other valuable consideration). In some embodiments, such sobriety tests (i) may be software driven, (ii) can be integrated as part of the online gaming experience, and/or (iii) may incorporate one or more of a variety of input devices, such as a keyboard, mouse, camera or microphone. In one non-limiting example consistent with one embodiment, between two games or rounds of a game a player may be asked to follow a moving object on their screen with their mouse (or otherwise) and a determination will be made based on the player's reaction time and/or motor skills. In another non-limiting example and consistent with an embodiment, a player may be asked to read a passage into a microphone, and a determination may be made based on the player's pronunciation (e.g., was the player slurring his words). In yet another example, a player may be asked to complete a task that tests the player's mental acuity.

In one or more embodiments, apparatus, systems, articles of manufacture and methods described herein provide for evaluating, analyzing or otherwise processing the results of an administered sobriety test. In some embodiments, part of such an analysis, evaluation or determination may comprise a decision as to whether to initiate a mediation event based on the results. Such an evaluation, analysis or other processing of the results of an administered sobriety test (as well as a decision based thereon) may be performed by software. In other embodiments, such an evaluation, analysis or other processing (as well as a decision based thereon) may be performed by a person (e.g., in conjunction with software).

In one or more embodiments, apparatus, systems, articles of manufacture and methods described herein provide for providing to online gamblers a portable testing device for facilitating in the administration of a sobriety test and/or for facilitating the transmission of results of a sobriety test in a secure manner to a remote entity (e.g., an employee or computing device of an online casino or an employee or computing device of a third party service for monitoring the sobriety of online gamblers). In some embodiments, such a portable testing device can be operatively connected (e.g., via a USB port) to a player's computer and/or operatively connected (e.g., via a communication line) to an online casino or other entity tasked with verifying the player's sobriety.

In accordance with some embodiments, once a player has completed a sobriety test, one or more of a variety of actions or mediating events may be taken or initiated if the player is determined to be unacceptably intoxicated and/or likely to be unacceptably intoxicated. Such a mediation event may be take or initiated by, for example, software installed on the player's computer, software of the portable testing device, software of a remote server computer (e.g., such as a computer of an online casino or a computer of a third party service for monitoring the sobriety of online gamblers) and/or a person monitoring and/or evaluating the results of sobriety tests administered to online gamblers.

A wide variety of mediation events are contemplated and described herein. For example, in one embodiment the player may not be allowed to gamble any more money. In another example, properties or characteristics of a game the player is currently playing (or plays during a current session or until the player illustrates through another sobriety test that he is not unacceptably intoxicated) may be modified or adjusted. For example, the amount that the player is allowed to wager, the difficulty of the game, the probabilities of winning, the size of the font, the number of warnings or instructions given to the player regarding risks that the player is taking, etc. Other example mediation steps and events are described below. Additionally, although embodiments herein are described in the context of determining if a player is intoxicated through consumption of alcohol, it should be understood that the embodiments may be applied to the detection of intoxication as a result of any use of drugs or otherwise to detect whether a player's judgment has been unacceptably impaired.

Certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

Although several embodiments, examples and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and it is possible that no single feature is solely responsible for its desirable attributes or is essential to practicing the inventions herein described.

B. Definitions

Throughout the description that follows and unless otherwise specified, the following terms may include and/or encompass the example meanings provided in this section. These terms and illustrative example meanings are provided to clarify the language selected to describe embodiments both in the specification and in the appended claims, and accordingly, are not intended to be limiting.

The term "intoxicated", as used herein, refers to a state of having one's judgment impaired due to intoxication from a chemical substance (e.g., alcohol or drugs) or otherwise, such that mental and/or visual acuity and/or physical coordination is unacceptable for a proposed activity.

A "sobriety test", as used herein, refers to a means or mechanism for determining or evaluating whether a player is intoxicated. In some embodiments, a sobriety test may comprise scoring or otherwise quantifying a level of intoxication of a player. In other embodiments, a sobriety test may be a qualitative (e.g., subjective) analysis that does not result in a quantifiable result.

The term "online casino", as used herein, refers to an entity or system of components which facilitates gambling by use of a network, such as the Internet, but may also encompass the facilitating of gambling by use of proprietary or closed networks (e.g., an intranet or wide area network) as well. For example, an online casino may be a website that accepts wagers and provides wagering games in a digital format over the internet.

A "wagering game", as the term is used herein, may comprise any game on which a player can risk a wager or other consideration, such as, but not limited to: slot games, poker games, blackjack, baccarat, craps, roulette, lottery, bingo, keno, casino war, etc.

As used herein, the term "network component" may refer to a user or network device, or a component, piece, portion, or combination of user or network devices. Examples of network components may include a Static Random Access Memory (SRAM) device or module, a network processor, and a network communication path, connection, port, or cable.

In addition, some embodiments are associated with a "network" or a "communication network". As used herein, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. Networks may be or include a plurality of interconnected network devices. In some embodiments, networks may be hard-wired, wireless, virtual, neural, and/or any other configuration of type that is or becomes known. Communication networks may include, for example, one or more networks configured to operate in accordance with the Fast Ethernet LAN transmission standard 802.3-2002® published by the Institute of Electrical and Electronics Engineers (IEEE). In some embodiments, a network may include one or more wired and/or wireless networks operated in accordance with any communication standard or protocol that is or becomes known or practicable.

As used herein, the terms "information" and "data" may be used interchangeably and may refer to any data, text, voice, video, image, message, bit, packet, pulse, tone, waveform, and/or other type or configuration of signal and/or information. Information may comprise information packets transmitted, for example, in accordance with the Internet Protocol Version 6 (IPv6) standard as defined by "Internet Protocol Version 6 (IPv6) Specification" RFC 1883, published by the Internet Engineering Task Force (IETF), Network Working Group, S. Deering et al. (December 1995). Information may, according to some embodiments, be compressed, encoded, encrypted, and/or otherwise packaged or manipulated in accordance with any method that is or becomes known or practicable.

In addition, some embodiments described herein are associated with an "indication". As used herein, the term "indication" may be used to refer to any indicia and/or other information indicative of or associated with a subject, item, entity, and/or other object and/or idea. As used herein, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

C. General Systems and Structure

FIG. 1A depicts a block diagram of an example system 100 according to some embodiments. The system 100 may comprise one or more remote gaming computers 106 in communication with a server computer 102 via a network 104. Typically a processor (e.g., one or more microprocessors, one or more microcontrollers, one or more digital signal processors) of a remote gaming computer 106 or server computer 102 will receive instructions (e.g., from a memory or like device), and execute those instructions, thereby performing one or more processes defined by those instructions. Instructions may be embodied in, e.g., one or more computer programs and/or one or more scripts.

In some embodiments a server computer 102 and/or one or more of the remote gaming computers 104 stores and/or has access to data useful for evaluating or determining whether an online gambler is intoxicated (e.g., by administering a sobriety test to the online gambler) and/or initiating a mediation event. Such information may include one or more of: (i) a sobriety test to be administered; (ii) rules defining whether, when and/or to whom to administer a sobriety test; (iii) results of sobriety tests previously administered to the online gambler in question; (iv) information relating to a game the online gambler is currently playing; (v) information relating to one or more portable testing devices 108 (e.g., an ISP address for such a device); and/or (vi) information relating to one or more mediation events that may be initiated.

A server computer 102 may comprise a computing device for administering or facilitating the administration of a sobriety test. For example, the server computer 102 may comprise a server computer operated by an online casino. In some embodiments, the server computer 102 may further be operable to facilitate a game program for a wagering game. In accordance with some embodiments, in addition to administering or facilitating the administration of sobriety tests, a server computer may comprise one or more computing devices responsible for handling online processes such as, but not limited to: serving the website to a player's computer, processing transactions, managing accounts, controlling wagering games, etc. In some embodiments, server computer 102 may comprise two or more server computers operated by the same entity (e.g., one server being primarily for administering sobriety tests for online gamblers and another server being primarily for providing wagering games to online gamblers).

In some embodiments, server computer 102 may include a sobriety testing system 110, which may comprise software, hardware and/or firmware for determining whether an online gambler is intoxicated. For example, a sobriety testing system 110 may comprise a program, associated databases or other files and hardware for (i) determining whether a sobriety test is to be administered to an online gambler; (ii) administering (or directing or causing another device to administer) a sobriety test; (iii) receiving, analyzing, evaluating and/or storing an indication of a sobriety test administered to an online gambler; (iv) initiating (or directing or causing another device to initiate) a mediation event based on a result of a sobriety test administered to an online gambler; and/or (v) receiving, evaluating, analyzing and/or storing a result of a mediation event. For example, in some embodiments an entity providing an online casino to online gamblers may operate a sobriety testing system for its online gamblers to determine whether the online gamblers are unacceptably intoxicated while gambling.

In some embodiments, a sobriety testing system 110 may be controlled and/or operated by an online casino or be another entity (e.g. a regulatory body, a law enforcement agency, a private corporation or another entity). Examples of processes that may be performed by a sobriety testing system 110 may include, but are not limited to: (i) selecting or otherwise determining an active player for whom to give a sobriety test; (ii) determining when to provide a sobriety test; (iii) storing data regarding one or more sobriety tests, one or more results of a sobriety test and/or one or more players; (iv) interrupting (directly or by directing or causing another device to interrupt) wagering activity; (v) providing (or causing or directing another device to provide) a sobriety test to a player of an online casino before and/or during a gaming session (e.g., by interrupting a wagering game or session or by integrating the test into the wagering game or session); (vi) processing, transmitting and/or evaluating the results of a sobriety test, (vii) allowing the player to start and/or continue participating in wagering activity, (viii) determining whether a player is intoxicated, and (ix) activating or initiating (or causing or directing another device to do so) one or more mediation steps for an intoxicated player.

Turning now to a description of a remote gaming computer 106, in accordance with some embodiments a remote gaming computer 106 may comprise a computing device that is operable to execute or facilitate the execution of a game program and used or useful by an online gambler for accessing an online casino. For example, a remote gaming computer 106 may comprise a computer workstation, laptop, mobile device, tablet computer, Personal Digital Assistant (PDA) devices, cellular or other wireless telephones (e.g., the Apple® iPhone™), video game consoles (e.g., Microsoft® Xbox 360™, Sony® Plasystation® 3, and/or Nintendo® Wii™), and/or handheld or portable video game devices (e.g., Nintendo® Game Boy® or Nintendo® DS™). A remote gaming computer 106 may comprise and/or interface with various components such as input and output devices (each of which is described in detail with respect to FIG. 2) and, in some embodiments, portable testing devices 108 (such as in accordance with embodiments described herein). A remote gaming computer 106 may be a dedicated gaming device (e.g., a slot machine) or a non-dedicated gaming device (e.g., an iPad™). It should be noted that a server computer 102 may be in communication with a variety of different types of remote gaming computers 106.

A remote gaming computer 106 may be used to play a wagering game over a network and transmit information relating to a sobriety test to be administered (or that has been administered) to an online gamblers. Any and all information relevant to any of the aforementioned functions may be stored locally on one or more of the client computers 106 and/or may be accessed using one or more of the client computers 106 (in one embodiments such information being stored on, or provided via, the server computer 102). In another embodiment, the server computer 102 may store some or all of the program instructions for determining whether to administer a sobriety test, administering a sobriety test and/or receiving and/or evaluating results of an administered sobriety test, and the one or more client computers 106 may access such information and/or program instructions remotely via the network 104 and/or download from the server computer 102 (e.g., a web server) some or all of the program code for executing one or more of the various functions described in this disclosure. It should be noted that the plurality of remote gaming computers 106 may each be located at the same location as the other remote gaming computers 106 and/or the server computer 102 or at another location. It should further be noted that while the server computer 102 may be useful or used by any of the remote gaming computers 106 to perform certain functions described herein, it need not control any of the remote gaming computers 106. For example, in one embodiment the server computer 102 may comprise a server hosting a website of an online casino.

A portable testing device 108 may comprise any device that is operable to communicate with a gaming device to administer or facilitate the administration of a sobriety test. Examples of a portable testing device may include, but are not limited to, a portable computing device (e.g., a PDA, a cell phone, a portable music device, a device dedicated to administering and evaluating sobriety tests) a cable, an adapter, a connector, a cartridge (e.g., a game cartridge), a disk (e.g., a 'floppy' disk, CD-ROM, DVD, mini-disk), a Static Random Access Memory (SRAM) device or module, a solid-state memory device, a flash memory device, a memory card device, and/or a network communication path, connection, port, and/or cable. In some embodiments, a portable testing device 108 may be coupled and/or removably coupled to a remote gaming computer 106 or portion thereof to facilitate communications therewith. A portable testing device 108 may be coupled via a connector to a Universal Serial Bus (USB) port of a remote gaming computer 106, for example. In some embodiments, a remote gaming computer 106 may be operable to administer or facilitate the administration of a sobriety test in the absence of a portable testing device 108, while in some embodiments a portable testing device 108 may be required to permit administration of a sobriety test. According to some embodiments, a portable testing device 108 may be comprised of various parts, portions, segments, and/or pieces. Some portable testing devices, for example, may comprise multiple portable testing devices coupled to and/or in communication with each other. Some portable testing devices 108 may comprise one or more components such as one or more: input devices, output devices, memory devices, processing devices, biometric devices, breath analyzer device, a blood testing device, a GPS devices, and/or encryption devices. In some embodiments, a portable testing device 108 includes software for administering or facilitating the administration of a sobriety test, which software may provide for encrypting and decrypting information transmitted from or received by the portable testing device 108.

As denoted by the dashed lines in FIG. 1A, in some embodiments a remote gaming computer 106 may be operable to communicate directly with server computer 102 rather than (or in addition to) through the network 104. As further denoted by dashed lines in FIG. 1A, in some embodiments a portable testing device 108 may be operable to communicate directly with server computer 102 rather than (or in addition to) through the network 104 and/or through a remote computing device 106.

In accordance with some embodiments, one or more of the remote gaming computers 106 may be operatively connected to a portable testing device 108. A portable testing device 108 may comprise a device for facilitating (i) determining whether to administer a sobriety test; (ii) administrating a sobriety test; (iii) evaluating and/or storing the results of a sobriety test; (iv) transmitting (which may in some embodiments include encrypting and/or decrypting information) an indication (e.g., results) of an administered sobriety test; (v) determining whether to initiate a mediation event; (vi) administering a mediation event; (vii) transmitting (which may in some embodiments include encrypting and/or decrypting information) an indication of an initiated mediation event; and/or (viii) receiving and/or transmitting instructions from an online casino and/or server computer 102.

In one embodiment, a server computer 102 may not be necessary or desirable. For example, some embodiments described in this disclosure may be practiced on one or more devices without a central authority. In such an embodiment, any functions described herein as performed by a server computer 102 and/or data described as stored on a server computer 102 may instead be performed by or stored on one or more remote gaming computers 106 and/or be a portable testing device 108. Additional ways of distributing information and program instructions among one or more remote gaming computers 106 and/or a portable testing device 108 will be readily understood by one skilled in the art upon contemplation of the present disclosure.

Figure 1B:
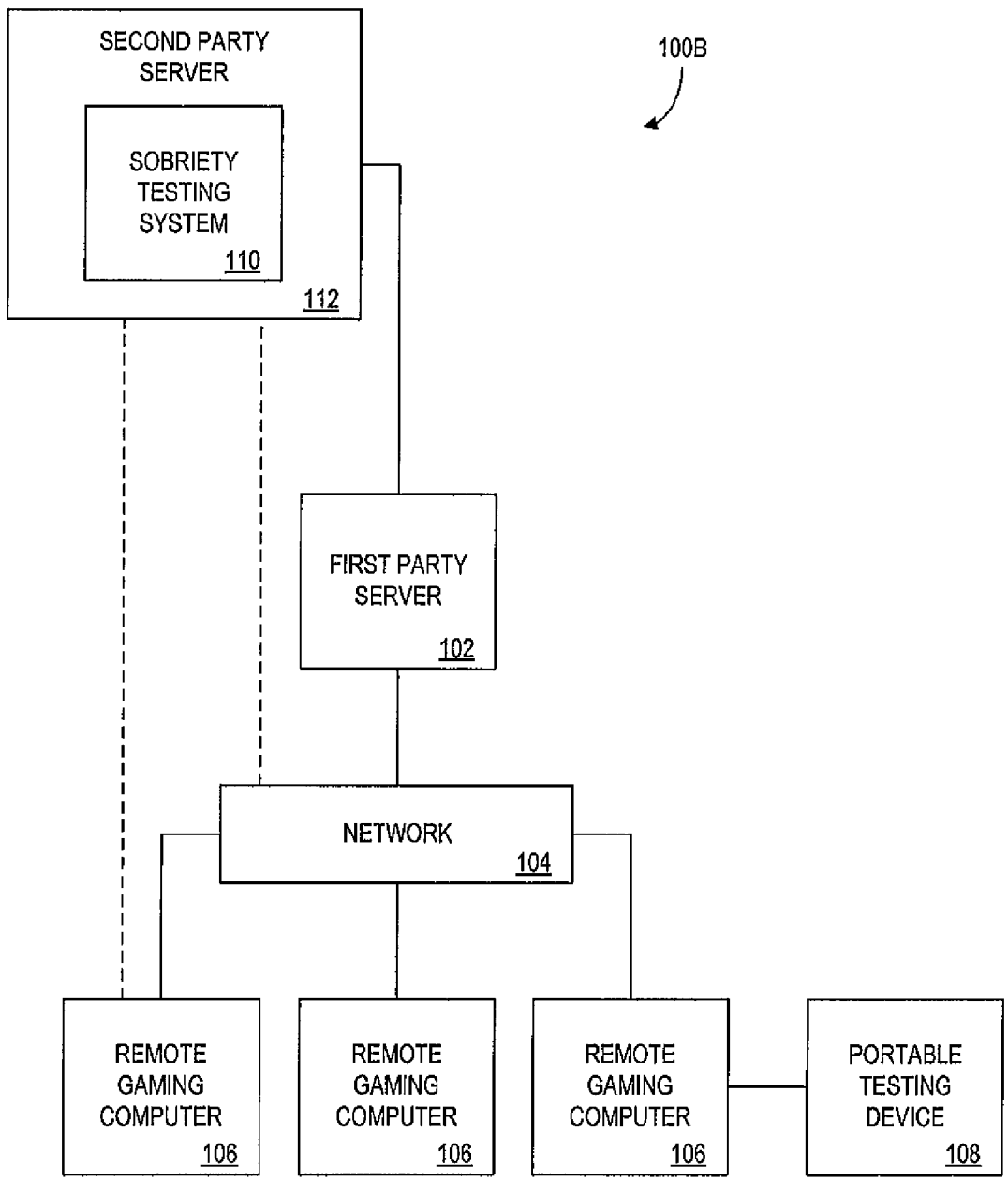
FIG. 1B is a schematic diagram of an embodiment of another system in accordance with one or more embodiments described herein.

FIG. 1B depicts a block diagram of another example system 100B according to some embodiments. The difference between example system 100A of FIG. 1A and system 100B of FIG. 1B is that there are two servers associated with two different entities: a first party server 102 and a second party server 110. The second party server 110 is illustrated as including a sobriety testing system 110 (as described in detail with respect to FIG. 1A) while the first party server does not. This is to illustrate that, in some embodiments, a sobriety testing system 110 may be operated by an entity distinct from the entity that operates an online casino (which may be operated by the first party operating first party server 102). For example, a regulatory body or private entity may operate a sobriety testing service that facilitates the administration of sobriety tests to online gamblers for a plurality of online casinos. In some embodiments, the first party server 102 may facilitate the administration of a sobriety testing system 110 but may not be primarily responsible for such. Thus, in some embodiments some of the functions described herein with respect to a sobriety testing system 110 may be performed by the first party server 102.

It should be noted that in some embodiments the second party server 112 may communicate directly (or via network 104) with one or more remote gaming computers 106 and/or a portable testing device 108, in addition to or in lieu of receiving and/or transmitting information to either of such devices via the first party server 102.

Figure 2:
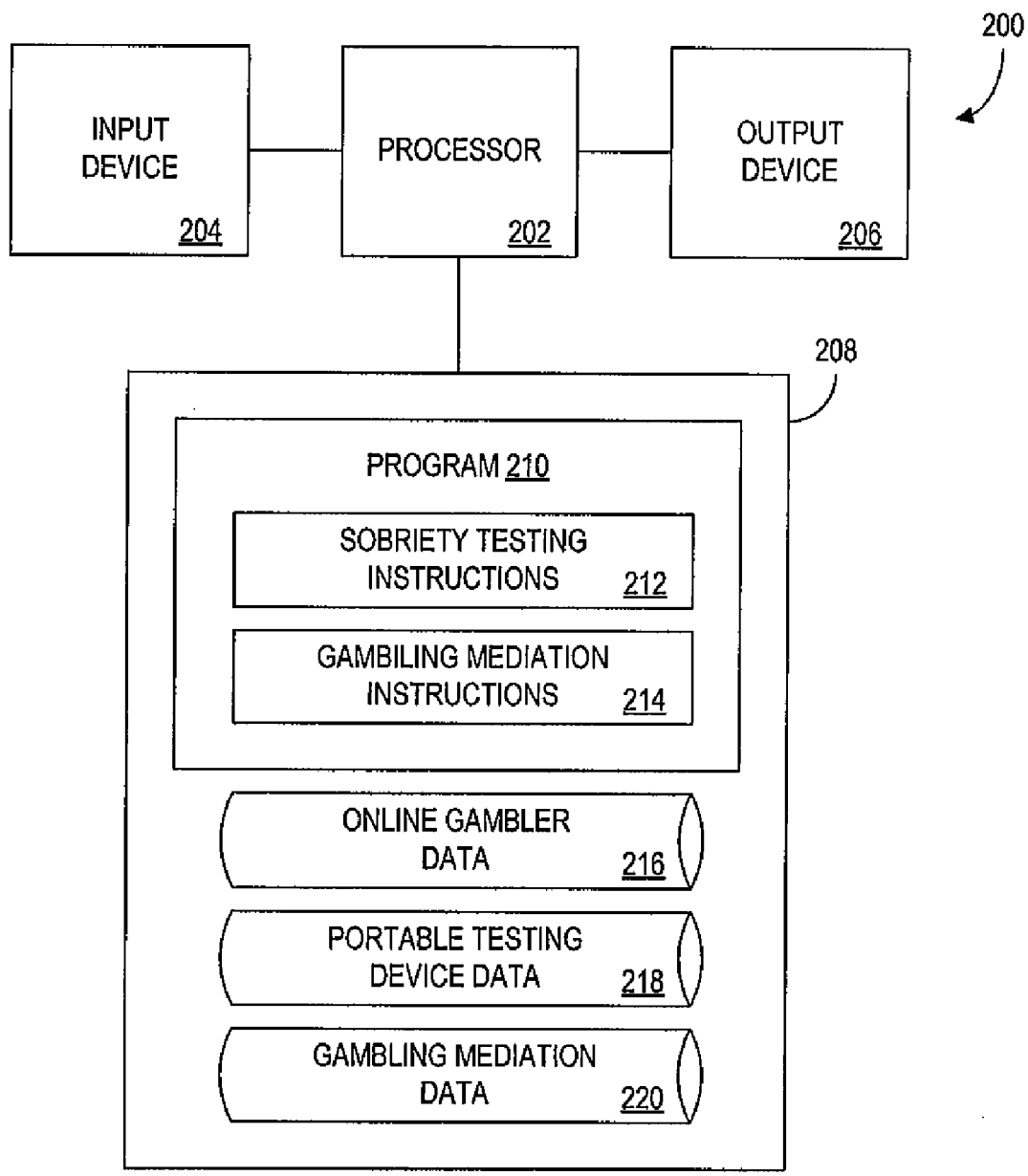
FIG. 2 is a block diagram of an embodiment of a computing device useful in a system according to one or more embodiments described herein, such as either the system of FIG. 1A or the system of FIG. 1B.

FIG. 2 is a block diagram of an apparatus 200 according to some embodiments. In some embodiments, the apparatus 200 may be similar in configuration and/or functionality to any of the remote gaming computers 106, the server computer 102, the server computer 112 and/or the portable testing device 108 of FIG. 1A and/or FIG. 1B. The apparatus 200 may, for example, execute, process, facilitate, and/or otherwise be associated with any of the processes 600, 700, 800 and/or 900 described in conjunction with FIG. 6, FIG. 7, FIG. 8 and/or FIG. 9, respectively, herein.

In some embodiments, the apparatus 200 may comprise a processor 202, an input device 204, an output device 206 and/or a memory device 208. Fewer or more components and/or various configurations of the components 202, 204, 206 and/or 208 may be included in the apparatus 200 without deviating from the scope of embodiments described herein.

According to some embodiments, the processor 202 may be or include any type, quantity, and/or configuration of processor that is or becomes known. The processor 202 may comprise, for example, an Intel® IXP 2800 network processor or an Intel® XEON™ Processor coupled with an Intel® E7501 chipset. In some embodiments, the processor 202 may comprise multiple inter-connected processors, microprocessors, and/or micro-engines. According to some embodiments, the processor 202 (and/or the apparatus 200 and/or other components thereof) may be supplied power via a power supply (not shown) such as a battery, an Alternating Current (AC) source, a Direct Current (DC) source, an AC/DC adapter, solar cells, and/or an inertial generator. In the case that the apparatus 202 comprises a server such as a blade server, necessary power may be supplied via a standard AC outlet, power strip, surge protector, and/or Uninterruptible Power Supply (UPS) device.

In some embodiments, the input device 204 and/or the output device 206 are communicatively coupled to the processor 202 (e.g., via wired and/or wireless connections and/or pathways) and they may generally comprise any types or configurations of input and output components and/or devices that are or become known, respectively.

The input device 204 may comprise, for example, a keyboard that allows an operator of the apparatus 200 to interface with the apparatus 200 (e.g., by a player, an employee or other worker affiliated with either an online casino or other entity operating a sobriety testing system). In some embodiments, the input device 204 may comprise a sensor configured to provide information such as an indication of a factor relevant to the intoxication of an online gambler, such information being provided to the apparatus 200 and/or the processor 202. For example, in an embodiment in which apparatus 200 comprises a remote gaming computer 106 or a portable testing device 108, input device may comprise a breathalyzer component. Other examples of input devices include, but are not limited to: a game controller and/or gamepad, a bar-code scanner, a magnetic stripe reader, a pointing device (e.g., a computer mouse, touchpad, and/or trackball), a point-of-sale terminal keypad, a touch-screen, a microphone, an infrared sensor, a sonic ranger, a computer port, a video camera, a motion detector, a digital camera, a network card, a Universal Serial Bus (USB) port, a GPS receiver, a Radio Frequency Identification (RFID) receiver, a RF receiver, a thermometer, a pressure sensor, and a weight scale or mass balance.

The output device 206 may, according to some embodiments, comprise a display screen and/or other practicable output component and/or device that is operable to output information. The output device 206 may, for example, provide instructions, guidance, questions or information to an online gambler (e.g., information relevant to a sobriety test being administered to the online gambler or a mediation event) or an employee or other worker affiliated with either an online casino or other entity operating a sobriety testing system (e.g., information relevant to a sobriety test and/or a mediation event). Some additional examples of output devices that may be useful in some embodiments include a Cathode Ray Tube (CRT) monitor, a Liquid Crystal Display (LCD) screen, a Light Emitting Diode (LED) screen, a printer, an audio speaker, an Infra-red Radiation (IR) transmitter, an RF transmitter, and/or a data port. According to some embodiments, the input device 204 and/or the output device 206 may comprise and/or be embodied in a single device such as a touch-screen monitor.

In some embodiments, the apparatus 200 may comprise any type or configuration of communication device (not shown) that is or becomes known or practicable. For example, the apparatus 200 may include a communication device such as a NIC, a telephonic device, a cellular network device, a router, a hub, a modem, and/or a communications port or cable. In some embodiments, the communication device may be coupled to provide data to a telecommunications device. The communication device 240 may, for example, comprise a cellular telephone network transmission device that sends signals (e.g., sobriety test and/or mediation event information) to a server (e.g., server 102 and/or server 112) in communication with a plurality of remote gaming computers 106. According to some embodiments, the communication device may also or alternatively be coupled to the processor 202. In some embodiments, the communication device may comprise an IR, RF, Bluetooth™, and/or Wi-Fi® network device coupled to facilitate communications between the processor 202 and another device.

The memory device 208 may comprise any appropriate information storage device that is or becomes known or available, including, but not limited to, units and/or combinations of magnetic storage devices (e.g., a hard disk drive), optical storage devices, and/or semiconductor memory devices such as Random Access Memory (RAM) devices, Read Only Memory (ROM) devices, Single Data Rate Random Access Memory (SDR-RAM), Double Data Rate Random Access Memory (DDR-RAM), and/or Programmable Read Only Memory (PROM).

The memory device 208 may, according to some embodiments, store a program 210 for facilitating one or more of the embodiments described herein, which program may include one or more of sobriety testing instructions 212 and/or one or more gambling mediation instructions 214. In some embodiments, the sobriety testing instructions 212 and/or the gambling mediation instructions 214 may be utilized by the processor 202 to provide output information via the output device 206.

According to some embodiments, sobriety testing instructions 212 may be operable to cause the processor 202 to administer (or facilitate the administration of) a sobriety test to an online gambler. For example, online gambler data 216 may be received via the input device 204 and/or the communication device and may, for example, be data mined, analyzed, sorted, filtered, decoded, decompressed, ranked, scored, plotted, and/or otherwise processed by the processor 202 in accordance with the instructions of sobriety testing instructions 212 and/or gambling mediation instructions 214 (e.g., in accordance with the method 600 of FIG. 6). In some embodiments, any information obtained by use of the sobriety testing instructions 212 and/or gambling mediation instructions 214 may be stored, analyzed, forwarded or otherwise utilized by the processor 202 (e.g., may be stored as online gambler data 216 and/or analyzed or forwarded to software and/or human personnel in accordance with sobriety testing instructions 212 and/or gambling mediation instructions 214). Such information may then be utilized for various purposes as described herein.

According to some embodiments, the sobriety testing instructions 212 may be operable to cause the processor 202 to prompt a device (e.g., a remote gaming computer 106 and/or a portable testing device 108) to determine whether to administer a sobriety test to an online gambler, select an online gambler to administer a sobriety test to, administer a sobriety test to an online gambler, determine a result of a sobriety test administered to an online gambler, or facilitate any of these functions. In some embodiments, the sobriety testing instructions 212 may be used by a human operator of a device to perform some or all of the above functions. The gambling mediation instructions 214 may, in some embodiments, utilize the online gambler data 216, the portable testing device data 218 and/or the gambling mediation data 220 to determine whether to initiate (or cause another device or operator of a device to initiate) a mediation event in response to a result of a sobriety test.

The apparatus 200 may function as a computer terminal and/or server of an online casino or other entity operating a sobriety testing system to receive and/or manage information related to sobriety tests administered to online gamblers. In some embodiments, the apparatus 200 may comprise a web server and/or other portal (e.g., an IVRU) that serves as an intake portal for sobriety test results. In some embodiment, the apparatus 200 may comprise a workstation or mobile device utilized by a live person who administers sobriety tests or reviews results of administered sobriety tests. In some embodiments, the apparatus 200 may comprise an apparatus that is operable to interact with an online gambler.

Any or all of the exemplary instructions and data types described herein and other practicable types of data may be stored in any number, type, and/or configuration of memory devices that is or becomes known. The memory device 208 may, for example, comprise one or more data tables or files, databases, table spaces, registers, and/or other storage structures. In some embodiments, multiple databases and/or storage structures (and/or multiple memory devices 208) may be utilized to store information associated with the apparatus 200. According to some embodiments, the memory device 208 may be incorporated into and/or otherwise coupled to the apparatus 200 (e.g., as shown) or may simply be accessible to the apparatus 200 (e.g., externally located and/or situated).

D. Databases

Referring to FIG. 3, a schematic illustration of an exemplary data structure 300 according to some embodiments is shown. In some embodiments, the exemplary data structure 300 may comprise a tabular representation illustrating an embodiment of a record of the online gambler data 216. The exemplary data structure 300 that is representative of a record of one embodiment of an online gambler data 216 includes a number of fields, each of which defines a gambling information related to an online gambler. Those skilled in the art will understand that the online gambler data 216 may include any number of entries. Those skilled in the art will further understand that many different and/or additional fields and/or types of data may be stored in the online gambler data 216 other than those illustrated as exemplary and non-limiting.

The exemplary data structure 300 of the online gambler data 216 defines the following fields: (i) a player name field 305, which stores a name of an online gambler, (ii) a player identifier field 310 which indicates a unique identifier for the online gambler and, in some embodiments, may serve as contact information for the online gambler (e.g., be the player's e-mail address), (iii) a normal sobriety score field 315 which indicates a normal or baseline sobriety score (score of a sobriety test administered to the player while the player was not intoxicated or was believed to be not intoxicated, which score is to serve as a baseline or threshold against which subsequent sobriety scores are compared to determine whether the player is intoxicated), (iv) a player status field 320 which indicates a status associated with the player (which status may, in some embodiments, be an indication of the player's level of intoxication and/or relevant to determining a mediation event to be initiated based on a current sobriety test score), (v) a first session identifier field 325 which identifies a first session engaged in by the player, (vi) a session time field 330 which indicates the start and end time for the first session identified in field 325, (vii) a testing time field 335 which at which a sobriety test was administered to the player during the first session identified in field 325; (viii) a sobriety test score field 340 which indicates the score obtained by the player when taking a sobriety test at the corresponding testing time; (ix) a second session identifier field 345 which indicates a second session engaged in by the player; (x) a session time field 350 which indicates the start and end time for the second session identified in field 345; (xi) a testing time field 355 which indicates a time at which a sobriety test was administered to the player during the second session identified in field 345; and (xii) a sobriety test score field 360 which indicates the score obtained by the player when taking a sobriety test at the corresponding testing time.

It should be noted that a wide variety of different types of sobriety tests may be administered and a wide variety of scoring mechanisms and formats may be utilized. The test score format illustrated in field 340 and 360 are exemplary only. The test score format illustrated in tabular representation 300 may be indicative, for example, of how many target events or tasks the player achieved successfully. For example, if a sobriety test comprises a set of questions, the sobriety test score may reflect how many questions the player answered correctly out of the total number of questions posed to the player. In another example, if a sobriety test comprises having the player repeat words, the sobriety test may reflect how many words the player repeated without slurring or otherwise mispronouncing out of the total number of words the player was asked to say. In yet another example, if a sobriety test comprises having a player track or trace an object or drawing on a screen with his mouse, the sobriety test score may reflect how many points of the object were targeted accurately by the player out of the total number of points on the object that were being assessed. In yet another example, if a sobriety test is to follow a moving object on the screen with a mouse, the sobriety test score may reflect the distance between the player's cursor and the object displayed. In yet another example, if the sobriety test is to select a series of objects appearing in succession or to strike keys on a keyboard in succession, then the sobriety test score may reflect the amount of time between selections or keystrokes. Of course, the format of a sobriety test score may vary and comprise, for example, a single number, letter or symbol (e.g., pass/fail or A, B, C scale), a percentage, a color scheme or any other format or mechanism desirable or practicable.

As described, in one embodiment, a result of a sobriety test may be evaluated on a pass/fail basis. If a player meets a standard or threshold performance, the player will be determined to have "passed". If the player does not meet required performance thresholds, the player may be determined to have "failed" the test. Failure of a test may cause one or more mediation events or other actions to be taken, as described herein. For example, if the test requires a player to follow a moving object around the screen with her mouse cursor, then the player may be determined to have failed if the mouse cursor falls outside of a threshold radius of the object (e.g., x number of pixels).

Embodiments, a player's performance of a test may be converted into a score, such as a numerical score. A variety of algorithms or mathematical equations can be developed or used with a selected testing method to determine a score. For example if a test requires a player to type a displayed sentence into a text field, then the test may be scored based on one (1) point for every typo and two (2) points for every second it takes to type the sentence. If the player exceeds a threshold number of points they may be determined to have failed. Pass/Fail status may be determined based on the score from one single test, on a cumulative score from two or more tests, on an analysis of a trend in test results from a player, based on a comparison of a test result to a baseline test result (the baseline test result being for that particular player or otherwise). Some example criteria for scoring performance may be, but not limited to: speed/time, accuracy, completion VS incompletion, etc.

The example data in tabular representation 300 may be utilized in some embodiments, for example, to determine whether a mediation event should be initiated. For example, a score achieved by a player during a current session may be compared to the player's baseline or normal score (e.g., as may be stored in field 315. If the player's current score is not within an acceptable range (e.g., not within a certain percentage, number of points, not on the same level, etc.) of the baseline or normal score, one or more mediation events (described in detail herein) may be initiated. For example, the player may be asked to retake the sobriety test, the player's gambling session may be paused or one or more parameters thereof may be modified and/or a message may be output to the player.

In some embodiment, in lieu of or in addition to the comparison of a current score being compared to a baseline or normal score, the trend in the player's sobriety test scores within a given session may be a factor upon which a determination is made as to whether to initiate a mediation event. For example, if the player's sobriety test scores within a session illustrate a more and more intoxicated state (e.g., player keeps getting fewer and fewer questions correct, player can trace an object less and less accurately and/or player is slurring more and more words), one or more mediation events may be initiated.

In some embodiments, in lieu of or in addition to the comparison of a current score being compared to a baseline or normal score, the trend in the player's sobriety test scores within a given session may be a factor upon which a determination is made whether and/or when to administer future sobriety tests. In other words, sobriety test scores may dictate the amount of time between testing within a given gambling session. For example, if the player's sobriety test score indicates that the player is nearer unacceptable intoxication than sobriety, then that score may cause the falls nearer the intoxication portion of a sobriety spectrum, then the player may be required to take another sobriety test in a short amount of time. In another example if the player's sobriety test score indicates that the player is not unacceptably intoxicated, then a there may be a longer period of time between tests.

In some embodiments, a status of a player (e.g., as illustrated in field 320) may be taken into account when determining whether to initiate a mediation event and/or which mediation event to authorize. For example, if a player has a status of "A" in some embodiments this status may indicate a problem gambler or a gambler with an alcohol problem and thus if a player with this rating has a certain score, a more severe mediation event may be initiated than if the player had another player status. In some embodiments, whether (and which) mediation event to initiate may be based on other information, such as information regarding the player's current gambling activity (e.g., magnitude and frequency of wagers, current profit/loss status of the session, volatility of the game being played, etc.).

Figure 4:
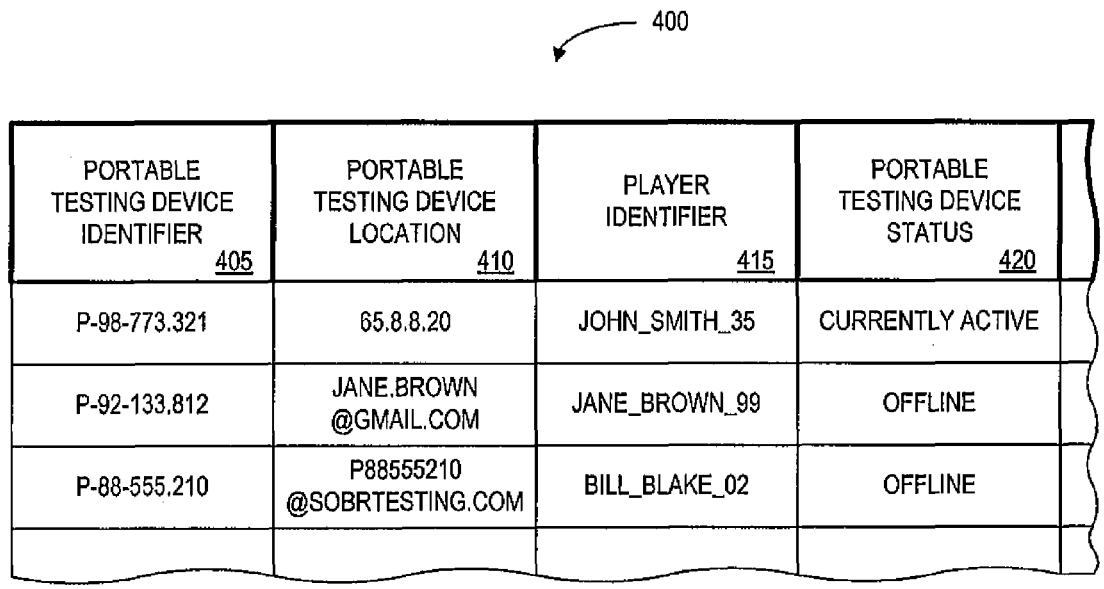
FIG. 4 is a table representative of one embodiment of a gambling mediation database according to one or more embodiments described herein.

Referring now to FIG. 4, a schematic illustration of an exemplary data structure 400 according to some embodiments is shown. In some embodiments, the exemplary data structure 400 may comprise a tabular representation illustrating an embodiment of the portable testing device data 218. The exemplary data structure 400 that is representative of the portable testing device data 218 includes a number of example records or entries, each of which defines a portable testing device which may be useful in facilitating sobriety tests in embodiments described herein. Those skilled in the art will understand that the portable testing device data 218 may include any number of entries. Those skilled in the art will further understand that many different and/or additional fields and/or types of data may be stored in the portable testing device data 218 other than those illustrated as exemplary and non-limiting.

The exemplary data structure 400 of the portable testing device data 218 defines the following fields: (i) a portable testing device identifier field 405; (ii) portable testing device location field 410; (iii) a player identifier field 415 which identifies a player associated with the portable testing device (in some embodiments more than one player may be associated with a single portable testing device); and (iv) a portable testing device status field 420.

The portable testing device identifier (405) may be a unique identifier which uniquely identifies the subject portable testing device. In some embodiments, a unique portable testing device identifier may be generated and/or assigned to a device when it is manufactured, sold or provided to a player. For example, in some embodiments a portable testing device may be provided to a player upon request, when a player registers with an online casino or other entity (e.g., local or federal regulatory body for regulating online gambling or private company for testing the sobriety of online gamblers). The portable testing device identifier may be stored in a database in association with a player identifier upon being provided to a player or upon a player registering the portable testing device with a service or entity which administers sobriety tests and/or collects information about administered sobriety tests. For example, portable testing devices may be made available for purchase to the public and be programmed to transmit its unique identifier to an online casino or other service or entity which administers sobriety tests and/or collects information about administered sobriety tests upon being registered or used in a gambling session.

The portable testing device location (410) may comprise information useful for communicating with or transmitting information to the portable testing device. For example, the portable testing device location may comprise an ISP address or an e-mail address of the portable testing device.

The portable testing device status (420) may indicate a current status of the portable testing device in terms of availability or use. For example, a status may indicate that the portable testing device is currently active (e.g., administering a sobriety test, transmitting and/or receiving data) or offline. In another example, the status may indicate whether a portable testing device is available for sale, has been sold, has been returned, has been registered and/or has been used.

It should be noted that a portable testing device, as illustrated in FIG. 1A and FIG. 1B, may comprise any of a variety of electronic devices which may be operatively connected to one or more of the remote gaming computers 106 and/or a server computer (e.g., server computer 102 and/or server computer 112), which server computers may be operating a sobriety testing system 110. Such portable testing devices may be operable to collect and/or transmit player information (e.g., information relevant to determining whether a player is intoxicated or otherwise has his judgment impaired). In some embodiments, a portable testing device may also be used to determine and/or communicate if a player is intoxicated. In some embodiments, a portable testing device may be operable to direct a remote gaming computer 106 to perform one or more functions (e.g., to transmit data, to adjust one or more parameters of wagering activity, to administer a sobriety test, etc.).

In some embodiments, a portable testing device may be provided (e.g., sold) to a player by an online casino, a regulatory agency, a private company or otherwise. For example, in some embodiments portable testing devices may generally be made available for sale to those members of the public who wish to participate in certain wagering activities. In some embodiments, a portable wagering device may be equipped with software which allows it to administer a sobriety test and/or facilitate the administration of a sobriety test (e.g., by communicating with a remote gaming computer).

In some embodiments, a portable wagering device may be equipped with software which allows it to receive information related to a sobriety test. For example, a portable testing device may be operable to receive information (i) from a remote gaming computer, indicative of a result of an administered sobriety test and/or (ii) from a server computer, indicative of a sobriety test to be administered to a player).

In some embodiments, a portable testing device may be equipped with software for transmitting information. For example, a testing device may be operable to transmit information (i) to a remote gaming computer, for directing the remote gaming computer to output information to a player in order to facilitate the administration of a sobriety test (and/or to obtain such information from a remote server computer; and/or (ii) to a server computer, such as a result of an administered sobriety test or information indicative of wagering activity engaged in by a player. For example, a portable testing device may be operable to monitor wagering activity engaged in by a player and determine whether an event for administering a sobriety test to a player has occurred.

In some embodiments, a portable testing device may be operable to administer a sobriety test directly to a player. For example, a portable testing device may comprise a breathalyzer and/or include a screen and/or microphone for outputting, to a player, information related to a sobriety test.

In some embodiments, a portable testing device may be operable to encrypt and/or decrypt information. For example, in embodiments in which a portable testing device transmits a result of an administered sobriety test to a server computer over a network, the portable testing device may first encrypt the result before the transmission.

In some embodiments, a portable testing device may be operable to download instructions or software from a remote server computer (e.g., from an online casino or other service operating a sobriety testing system) and/or facilitating such downloading to a remote gaming computer to which the portable testing device is coupled or in communication with. For example, in some embodiments a portable testing device may be operable to be attached to a remote gaming computer via any number of available means, such as using a USB port, a Wifi connection (e.g., 802.11 ee), a Bluetooth wireless connection. Upon being so attached or plugged in, the portable testing device may install software onto the remote gaming computer which facilitates the administration of sobriety tests to a player using the remote gaming computer for online gambling.

In one or more embodiments, a portable testing device may be useful for purposes other than facilitating a sobriety test. For example, a portable testing device may also be used to determine a player's location, and to submit that information to an online casino, regulatory agency or other entity. This information may be used for any of a variety of reasons such as to determine that a player is in a jurisdiction that allows gambling. In another example, the information may be used to make sure that the game conforms to local jurisdictional requirements. Location information may be acquired using any of a variety of known methods, such as cell tower triangulation or GPS.

Figure 5:
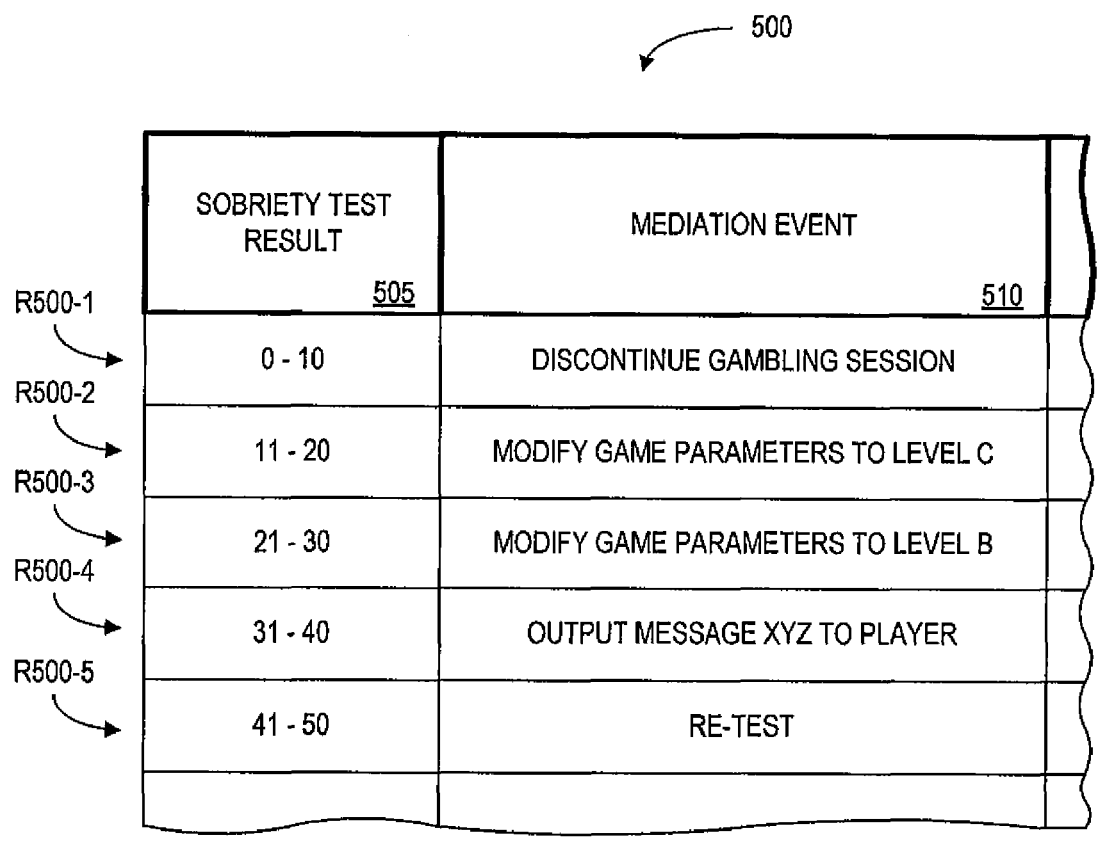
FIG. 5 is a table representative of one embodiment of a portable testing device database according to one or more embodiments described herein.

Turning now to FIG. 5, a schematic illustration of an exemplary data structure 500 according to some embodiments is shown. In some embodiments, the exemplary data structure 500 may comprise a tabular representation illustrating an embodiment of the gambling mediation data 220. The exemplary data structure 500 that is representative of the gambling mediation data 220 includes a number of example records or entries, R500-1 through R500-5, each of which defines a mediation event which may be initiated in response to a certain corresponding result of a sobriety test administered to an online gambler. Those skilled in the art will understand that the gambling mediation data 220 may include any number of entries. Those skilled in the art will further understand that many different and/or additional fields and/or types of data may be stored in the gambling mediation data 220 other than those illustrated as exemplary and non-limiting. The exemplary data structure 500 of the gambling mediation data 220 defines the following fields: (i) a sobriety test result field 505; and (ii) a mediation event field 510. The sobriety test result field 505 illustrates a range of sobriety test scores for each record.

It should be understood that other arrangements or formats of sobriety test results may be used. For example, a test result comprising a single digit, number, symbol, or other indicator may be used. In another example, tests results may be binary, for instance 2 results—"pass" and "fail". In another example, a test result comprising a prose or other text description may be used. In yet another example, a test result comprising an audio tone or other visual representation may be used. In summary, any manner of conveying a result, magnitude (or relative magnitude) or level of sobriety test result may be used.

Similarly, although the mediation event field 510 illustrates a text description/summary of a mediation event, any other format or mechanism for associating a mediation event (or plurality of mediation events or mediation mechanism) with a sobriety test result may be used. For example, in some embodiments the mediation event field 510 may store an identifier, file and/or file path for a mediation event. In another example, the mediation event field may include an instruction or file that may be downloaded or otherwise transmitted or communicated (e.g., via FTP transmission or an e-mail) to a device that is to facilitate a particular mediation event.

As noted herein, in some embodiments factors other than a sobriety test result, such as that depicted in field 505, may be used in determining whether and which mediation event to undertake (in addition to or in lieu of a sobriety test score). For example, a baseline or previously obtained sobriety test result for a particular player, a status of the player, a current or past wagering history or pattern of the player and the status, wagering activity and/or sobriety test results of one or more other players may be taken into account. For example, a certain status rating or wagering history or pattern of a player may indicate that this player, whose sobriety test score or other result appears to indicate that the player is intoxicated, has in the past wagered while intoxicated but without incurring unusually large debts, engaging in highly risky or detrimental wagering activity or otherwise posing a risk to himself or others due to his wagering activity. In another example, if it appears that a player is taking more risks, playing at a different time than he has previously played, playing at a higher frequency and/or placing higher wagers than the player has previously made, it may be determined that the player may be intoxicated, with or without taking into account the results of a sobriety test. In some embodiments, any and all such factors may be taken into account in determining whether to administer a sobriety test to an online gambler (e.g., if a player is placing higher wagers more frequently and/or playing in the middle of the night when he previously hasn't, this wagering activity may trigger the administration of a sobriety test to the online gambler).

In one example described above, a mediation event may be initiated in response to determining that one or more characteristics of a particular period of play satisfies a predetermined criteria. For instance, a sobriety test may be administered to a player based on wagering patterns that deviate from the normal or typical wagering patters of that player (or average players). In such an example, certain characteristics of gambling activity may be stored in a database and associated with the player's unique identifier. For instance, referring again to FIG. 3, example tabular representation 300 may include a variety of gambling activity data, including amounts wagered, date and time of wagers, game played, wager type, a number of consecutive wagers placed, the amount of time between wagers, bonus rounds played, an amount of money lost for each wager, an amount of money won for each wager, an amount of money won for a set of wagers, an amount of money lost for a set of wagers, date and time of a set of wagers. Such data may be stored in relation to a comprehensive history of the player's activity, or data may be broken into segments, such as that corresponding to the beginning and an end of a particular period of gambling. Computer generated comparisons of data or sets of data may then be used to determine whether or not to perform a mediation event, such as administering a sobriety test, contacting a third party, or suspending play.

The functions of administering a sobriety test and/or determining whether to administer a sobriety test (or to whom it should be administered) may be performed by a variety of entities and/or devices. Similarly, the functions of determining a mediation event and/or whether a mediation event should be undertaken may be performed by a variety of entities and/or devices. For example, an operator of a sobriety testing service or program (e.g., an online casino or other private company, a regulatory agency and/or any affiliate thereof), referred to as an "operator" herein, may perform any, all or part of any of the foregoing functions. In another example, any of the devices described with respect to FIG. 1A and FIG. 1B may perform any, all or part of any of the foregoing functions.

As described herein, in some embodiments a certain sobriety test result (e.g., a sobriety test score that is within a predetermined range of scores), when obtained by a player to whom the sobriety test was administered, may cause a certain corresponding mediation events to be undertaken (e.g., applied to the player) by an operator and/or device described herein. For example, in certain severe circumstances the player's online gambling activity may be discontinued or suspended (e.g., for some predetermined period of time and/or until the player achieve a satisfactory sobriety test result that qualifies the player to resume his gambling activities). For example, as described, in some embodiments a sobriety test may be administered to determine whether a player is intoxicated or otherwise has his judgment unacceptably impaired and, if it is determined in accordance with the results of the sobriety tests that the player does so have his judgment impaired, then one of the following mediation events might be undertaken by an operator and/or device described herein in order to address the potential issue:

(i) The player may be contacted (e.g., by personnel of the operator). For example, live personnel may contact the player (e.g., by talking to the player (e.g., using a phone line or over an internet connection, such as using VoIP) and/or viewing video footage of the player taken via a webcam or otherwise obtained to determine or verify whether the player is unacceptably intoxicated and/or to intervene in the player's wagering activity.

(ii) The player may be prompted and/or required to call the casino (e.g., within a relatively short time frame, such as within the next 60 seconds), and may not be allowed to continue gambling until they have done so. For example, a message including a toll free number for the player to call may be output (a transaction number or other unique code or identifier may be also output to the player to provide upon calling, such number or code being related to the player's sobriety test result which prompted the current mediation event).

(iii) The player's wagering activity may be paused for a predetermined period of time (e.g., an hour), either at a site remote from the player (e.g., a server hosting an online casino wagering game may be directed to disallow the player's wagering activity) or at a device local to the player (e.g., the player's remote gaming computer may be directed to pause the player's wagering activity, by a remote server, software installed on the remote gaming computer and/or a portable testing device).

(iv) The player may be given another (or multiple) sobriety test immediately when logging in the next time or upon the previous sobriety test result having been received, to verify the previous sobriety test result and to verify that the player does appear to be unacceptably intoxicated. Such follow-up sobriety tests may be of the same kind as a previously administered sobriety test or of another kind. For example, if the player scored poorly on a sobriety test which tested the player's mental acuity, the player may be asked to take a sobriety test which tests the player's physical coordination.

(v) A message (e.g., warning or information) may be output to the player, via a display or speaker of a device. For example, it may be suggested that the player stop, pause or modify his wagering activity (e.g., decrease his wager amounts or frequency) and/or that the player not drink alcohol while playing. In another example, an offer may be made to the player for a benefit that can only be used in the next x amount of time (e.g., "come to our restaurant and get a free meal", "play another game (with less volatility) and get double your buy in", "try session based gaming with capped losses!"

(vi) One or more parameters of the player's wagering activity may be modified. For example, wagering limits such as one or more of the following may be introduced into the player's wagering session: cannot wager more than $x/per game or per time, cannot make more than x wagers/y time, prohibit games of certain types (e.g., the player may only be permitted to play slots, side bets, extra bets, more than one bet or bonus rounds may be eliminated, games of a certain volatility or complexity).

(vii) The player may be prevented from making any additional buy-ins for the current wagering session—the player may be prevented from adding to their account balance.

(viii) One or more features of the game or of the game's display may be modified. For example, the visual layout of the game may change, new data may be tracked (and displayed), and/or distracting sounds or visuals (e.g., bells, animations) may be eliminated.

(ix) One or more entities may be contacted. For example, the administrator of the sobriety test may send a message (e.g., an email, a sms message, an mms message, a phone call) to an operator, the player, or someone associated with the player (e.g., a spouse, friend, relative).

E. Processes

Figure 6:
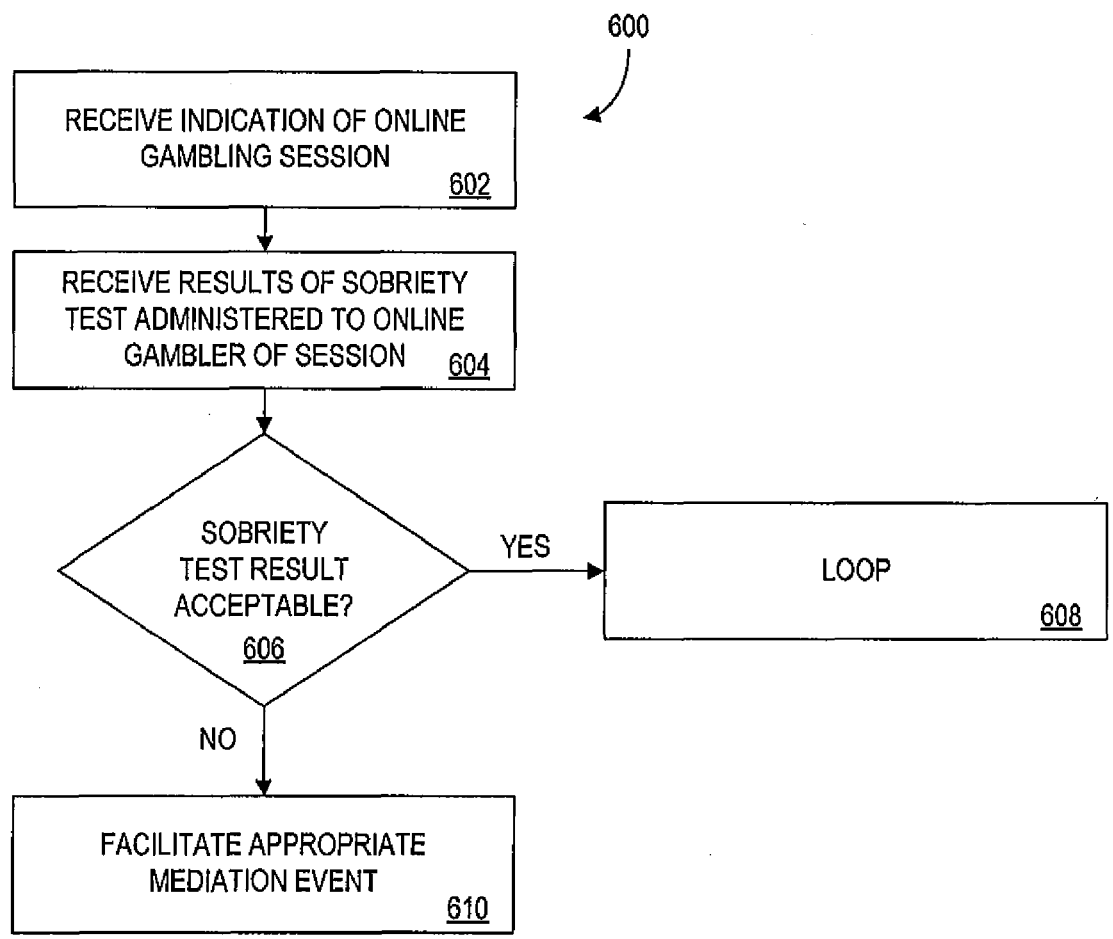
FIG. 6 is a flowchart illustrating a method according to one or more embodiments described herein.

Referring now to FIG. 6, a flow diagram of a method 600 according to some embodiments is shown. The method 600 may, for example, be performed by or on behalf of an operator of a sobriety testing service. For purposes of brevity, the method 600 will be described herein as being performed by a server computer 102 (e.g., a server computer operated by an online casino). However, in other embodiments some or all of the steps may be performed by another device (e.g., a portable testing device 108 and/or a remote gaming computer 106). It should further be noted that while all of the steps described with respect to method 600 may be performed by a single device, in some embodiments different steps may be performed by different devices. Further any steps described herein as being performed by a particular computing device may be performed by a human or another computing device as appropriate.

According to some embodiments, the method 600 may comprise receiving an indication of an online gambling session (602). For example, it may be determined that a player has logged onto an online casino and initiated a gambling session. An identifier of the player (e.g., selected by the player upon logging on or when previously registering with the online casino or other entity) may be provided by the player. Thus, step 602 may in some embodiments include receiving an identifier of the player participating in the gambling session. In some embodiments, step 602 may comprise detecting (e.g., by a remote gaming device and/or a portable testing device) that a player has logged onto an online casino website and begun wagering. In some embodiments, step 602 may comprise detecting that a player has placed a wager on an online casino game or accessed an account of funds available for wagering on an online casino game.

As described herein, in accordance with some embodiments, the sobriety of players playing wagering games through an online casino may be tested using one or more of the testing methods described herein. In one embodiment, all players playing a wagering game may be required to complete a sobriety test at least once during each gaming session. Herein, a "session" or a "gaming session" refers to a period of time spent by a player on a gambling website, which may be defined in any number of ways, such as, but not limited to: from the time a player logs into an online casino to the time at which the player logs out; from the time a player arrives at an online casino's website to the time the player leaves that website, an amount of time specified by the online casino (e.g., an hour, a day, a week), from the time a player establishes a credit balance to the time the player cashes out the credit balance, from the time a player initiates a wagering game to the time the player indicates a desire to finish playing the wagering game, a specified number of rounds of a game, etc.

The results of a sobriety test administered to the player participating in the online gambling session are received in step 604. For example, a score of a sobriety test may be received, such as a result of a breathalyzer test or a visual or mental acuity test. In some embodiments, receiving a result of a sobriety test may comprise receiving a score achieved in the sobriety test. In other embodiments, receiving a result of a sobriety test may comprise receiving audio, text or video information associated with the player (e.g., video footage of the player playing the online wagering game, audio of the player speaking into a microphone, observations or opinions of personnel who viewed, listed to or interacted with the player). In some embodiments, the results of the sobriety test may be received in encrypted form.

In step 606, it is determined whether the sobriety test result test is acceptable. This may comprise, for example, analyzing the result to determine whether it indicates that the player is unacceptably intoxicated. In some embodiments, the result received in step 604 may comprise raw data that needs to be analyzed or evaluated to determine a score or final output based upon which a determination is made as to whether the player is unacceptably intoxicated. In other embodiments, at least some of such analysis or evaluation may already have been performed such that the output of the analysis or evaluation is received in step 604 (with or without the raw data upon which the output was determined). In some embodiments, step 606 may comprise determining whether the result obtained in step 604 corresponds to a mediation event. In some embodiments, step 606 may comprise determining whether the result received in step 604 is readable or usable (e.g., not corrupted, been tampered with or in an unreadable format).

If it is determined in step 606 that the sobriety test is acceptable (i.e., indicates that the player is not unacceptably intoxicated), the process 600 moves to step 608, wherein the process loops until another sobriety test result is received. If it is determined that the sobriety test result is not acceptable (i.e., the player is unacceptably intoxicated), the process flows to step 610, wherein an appropriate mediation event is facilitated. For example, a predetermined mediation event may be undertaken or a database may be consulted as to which available mediation event is to be undertaken.

Figure 7:
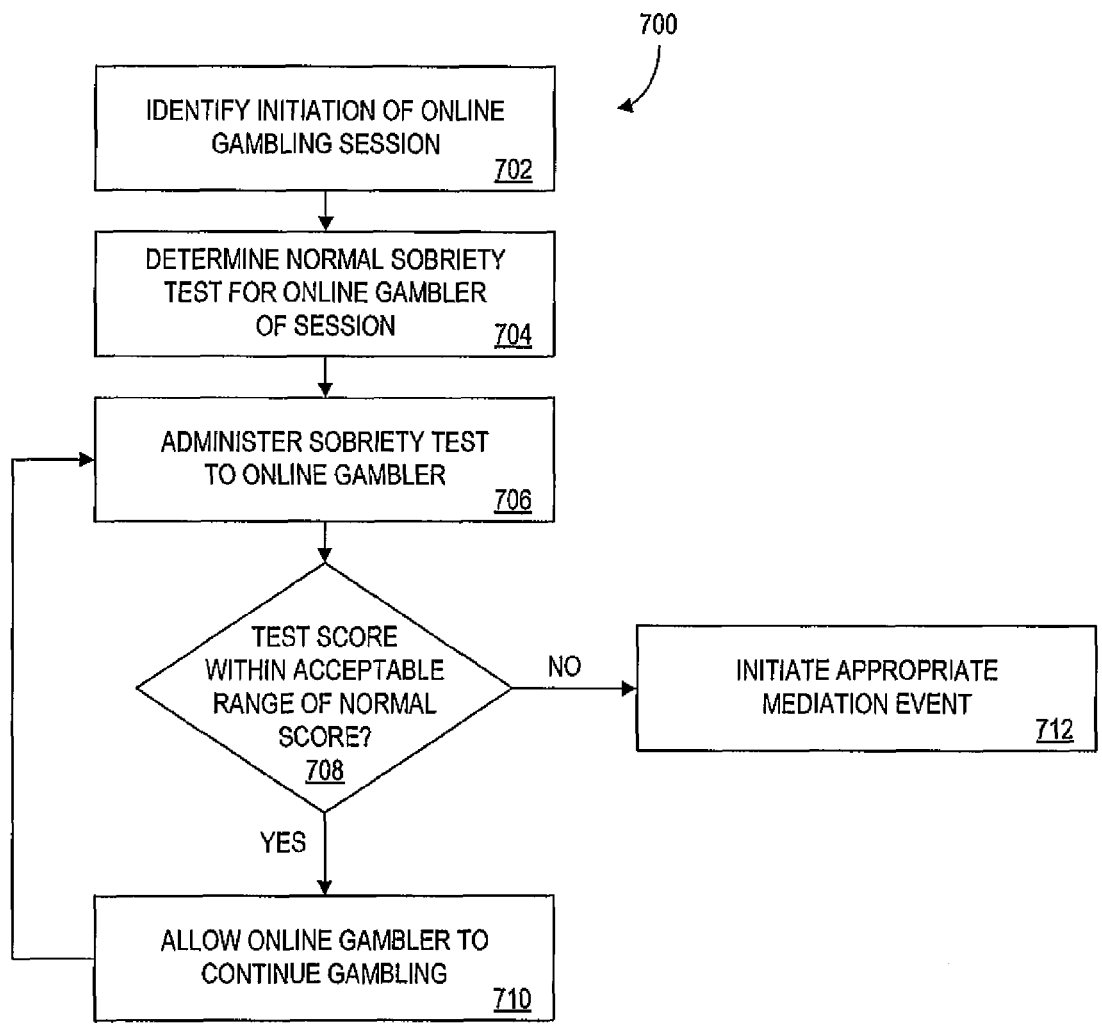
FIG. 7 is a flowchart illustrating a method according to one or more embodiments described herein.

Turning now to FIG. 7, a flow diagram of a method 700 according to some embodiments is shown. The method 700 may, for example, be performed by or on behalf of an operator of a sobriety testing service. For purposes of brevity, the method 700 will be described herein as being performed by a server computer 102 (e.g., a server computer operated by an online casino). However, in other embodiments some or all of the steps may be performed by another device (e.g., a portable testing device 108 and/or a remote gaming computer 106). It should further be noted that while all of the steps described with respect to method 700 may be performed by a single device, in some embodiments different steps may be performed by different devices. Further any steps described herein as being performed by a particular computing device may be performed by a human or another computing device as appropriate.

According to some embodiments, the method 700 may comprise determining an initiation of an online gambling session (step 702). This may be similar to step 602, described with respect to FIG. 7.

The normal sobriety test score for an online gambler of the session is then determined (step 704). For example, a baseline score associated with the player may be retrieved from memory (e.g., such as from a database such as the example tabular representation 300 illustrated and described with respect to FIG. 3). A normal sobriety test score may have previously been obtained from the player when the player first registered with an online casino or operator of a sobriety testing service and at a time it was believed (e.g., based on a representation of the player and/or verification of an employee of the operator) that the player was not intoxicated. Thus, in some embodiments a standardized threshold of performance may be used to determine if a player passes a currently administered sobriety test. For example all players must achieve a score of 10 or higher. In another example, all players may have to complete a test in a specified time.

As described, in some embodiments in an attempt to judge performance relative to a player's motor or cognitive skills when sober, a player may be required to perform a test while sober in order to provide a baseline for comparison when the player is provided a sobriety test in the future. For example, a player may be given a sobriety test one or more times when they are registering for an account with an online casino or other entity. The score that that player achieves (e.g., for a single test or an average score for a plurality of instances of the test) while registering may be used as a point of reference when the player takes a sobriety test when gambling in the future.

The following example illustrates one useful aspect of a system that utilizes a comparison of a baseline score to a current score for a sobriety test: assume that Mork scores a 60 during baseline testing, and Mindy scores a 25. These scores are stored in a database along with the player's profiled on the Casino Server or the Sobriety Testing Controller. If both players are given the test later on and both score a 30, then Mindy may pass when comparing that score relative to the original 25. However, Mork may be determined to have failed when comparing the 30 to the original 60.

To help ensure that the baseline tests are accurate, and minimize the risk that players are intentionally scoring poorly, baseline testing may be performed discreetly, e.g., without notifying the player why they are taking a test or even that they are taking a test. Additionally, players may be required to re-take a baseline tests periodically or otherwise to account for any improvement in skill that may occur over time or repeated exposure to a test.

In step 706, a sobriety test is administered to the online gambler participating in the online gambling session identified in step 702. As described herein a wide variety of sobriety tests may be administered in order to determine whether a player is unacceptably intoxicated. The actual sobriety test may take one of many forms, and in fact, many different kinds of tests may be used by a single online casino or other entity administering the sobriety test(s). For example, the test that a player receives a first time may be somewhat or completely different than when the player receives a sobriety test a second time. Of course, players may be given the same sobriety test(s) every time in order to more easily track changes in results. Since temporary degradation of motor and cognitive skills are symptoms of intoxication, any task or test that can be used to test such skills can be employed to determine if a player is intoxicated. Therefore, although a number of examples are provided herein, the list of examples should not be thought of as limiting—there may in fact be other types of tests that exist that would work well in such a system. Additionally, the word "test" is used to describe any method used to determine if a player is intoxicated or otherwise has his judgment impaired. Therefore, in some embodiments herein, the term "test" may simply describe the submission of player data or input, the results of an analysis performed on recorded player input, or the completion of a task requested of an online player.

Any one or more of the following example tests may be used by a sobriety testing system to determine if a player is intoxicated or otherwise has his judgment impaired. As stated earlier, some of the "tests" are simply data recording and analysis, and some are actual tasks that the player must complete. Example sobriety tests:

(i) Tracing—Players may be required to use an input device such as a touch screen, arrow keys, mouse, etc. to trace or follow an object on the screen. For example, a player may have to trace a line that zig zags across the display. Similarly, the test may require the player to follow a moving object around the display screen. For example, the player may be required to follow a dot that moves around the screen for a predetermined amount of time.

(ii) Puzzles—a variety of puzzles or "brain teasers" may be used to determine a player's cognitive speed. For example, a player may be asked to complete a virtual jigsaw puzzle (e.g., a player may be required to re-assemble an image using pieces of the image). Word problems or simple equations may be used to judge how quickly a player's mind is working.

(iii) Basic Math Problems—a player may be asked to answer a string of equations such as: (5+5), (2*10), (16/4), etc.; a player may be required to determine the sum of the value of two or more playing cards; a player may be asked to subtract the value of one die from the value of another die; a player may be asked to answer: "Sonny has 12 apples, and he gives 2 to Cher and is given 5 more by Ozzie. How many apples dos Sonny end up with?"

(iv) Sequence problems—the player may be asked to complete the sequence of a pattern or to evaluate items of a list based on some criteria. For example: "1,3,5,7—what number comes next in the sequence?" In another example: "Which doesn't belong? Apple, Orange, Banana, Psycho Baboon." In yet another example: "order the following objects from largest to smallest, or from darkest to lightest."

(v) General Knowledge Questions—Players may be asked to answer one or more questions testing general knowledge. For example, "What color is the sky?" or "How many arms to Humans Have?"

(vi) Voice Samples—Players may be asked to repeat an audio phrase or read a phrase from a screen. Players may do so by speaking into a microphone or calling a specified phone number. This file may be evaluated by software that determines the likelihood of whether or not a player is unacceptably intoxicated (e.g., by looking for slurred speech, stammering, words left out, etc.).

(vii) Word Repetition—a player may be asked to repeat or read a specific type of language. For example, the phrase may be a tongue twister. In another example, the words may be nonsensical and the player has to sound them out. In another example the words may actually be in a language other than the player's native language.

(viii) Typing Samples—A player may be asked to type a phrase or paragraph into a text box. The player's ability may be judged based on the rate at which the player types or the amount of mistakes he or she makes while typing. Typing may be evaluated by software and in real time to pick up on the amount of times a player had to erase a mistyped letter or word.

(ix) Images and Expressions—Still or Video images of a player may be taken (e.g., at random intervals) using a web cam or other camera device connected to the Sobriety Testing Controller. These images may be evaluated by software and/or human personnel to determine if a player is intoxicated.

(x) Other visually observable traits of the player—if a player exhibits characteristics or mannerisms that are generally considered traits of being intoxicated, such as, leaning, problems focusing, etc. A computer may also be programmed to learn the mannerisms of a drunk person and then monitor for them. In another example, the color of the player's complexion may be evaluated to determine if they are flushed, which is a common trait in intoxicated people.

(xi) Players' eyesight characteristics—one or more characteristics of the player's eyes may be evaluated for signs of intoxication. For example, the size of a player's pupils may be evaluated. In another example, the player's ability to follow a moving object with her eyes may be evaluated. For example, the player may be asked to follow a dot across the screen. If the player cannot follow it, their eyes twitch or have trouble focusing, then they may be considered intoxicated.

(xii) Modified Game Screen—The game screen that is presented to a player may periodically alter. For example, the submit or "spin" button may move around on the screen. The amount of time it takes a player to realize the difference may be monitored. For example, if they continuously click the same spot after a button has been moved, they may be considered intoxicated. Similarly, if it takes the player a long time to begin the next game (assumedly because they cannot find the button) then a player may be considered intoxicated.

(xiii) Game Play Characteristics—a player's performance in a game may be monitored and used to determine if the player is intoxicated (this may include comparing one or more of such characteristics to characteristics displayed in one or more previous sessions). The following is a list of the types game play characteristics that may be evaluated, although others may be used as well: rate of play or time between games, the magnitude of the wagers made, a change in patterns of play, a sudden strings of losses.

(xiv) Submissions from a Portable Testing Device—A portable device may be used to receive and/or transmit player input that can be used in determining if a player is intoxicated. Such a device may be connected to remote gaming computer being used by a player to participate in an online gaming session, or directly to the a sobriety testing system using any known methods of communication, such as but not limited to a telephone network, a cellular network, a wireless internet connection, etc. For example, a portable breathalyzer may be fitted with a processor and connected to a remote gaming computer through a port such as a USB port. The player may be required to submit readings from the breathalyzer at periodic intervals or the breathalyzer may be programmed to do so. In one embodiment, the breathalyzer may output a code that must be input by the player into a text box provided on the Online Casino website or via a telephone connection.

It should be noted that in some embodiments players may be notified that they are taking a sobriety tests or that a sobriety test is being administered to them while in other embodiments the players are not so notified. For example, in some embodiments a player to whom a sobriety test is being administered may be given information about why they are taking the test, any related consequences and instructions for how to take the test. In another embodiment, the player may not be notified or informed that he or she is taking a test (e.g., the test may be integrated into the game in a manner that makes it virtually unnoticeable to the player). For instance, the test may be presented as a bonus game or as a feature of the game itself (e.g., clicking a moving button to submit a wager). Additionally, in one embodiment, sobriety tests may be optional. In another embodiment sobriety tests may be mandatory. In such an embodiment, the player may not be allowed to continue gambling (or not allowed to continue gambling for real money) until he or she successfully completes the sobriety test.

Returning now to FIG. 7, in step 706 it is determined whether a sobriety test score of a sobriety test administered to the player in step 704 is within an acceptable range of the player's normal sobriety test score. If it is, the online gambler is allowed (step 710) to continue his current gambling session (e.g., until it is determined that another sobriety test should be administered to the player). Otherwise, an appropriate mediation event is initiated in step 712. Various mediation events and how one can be selected as an appropriate one are described herein.

Figure 8:
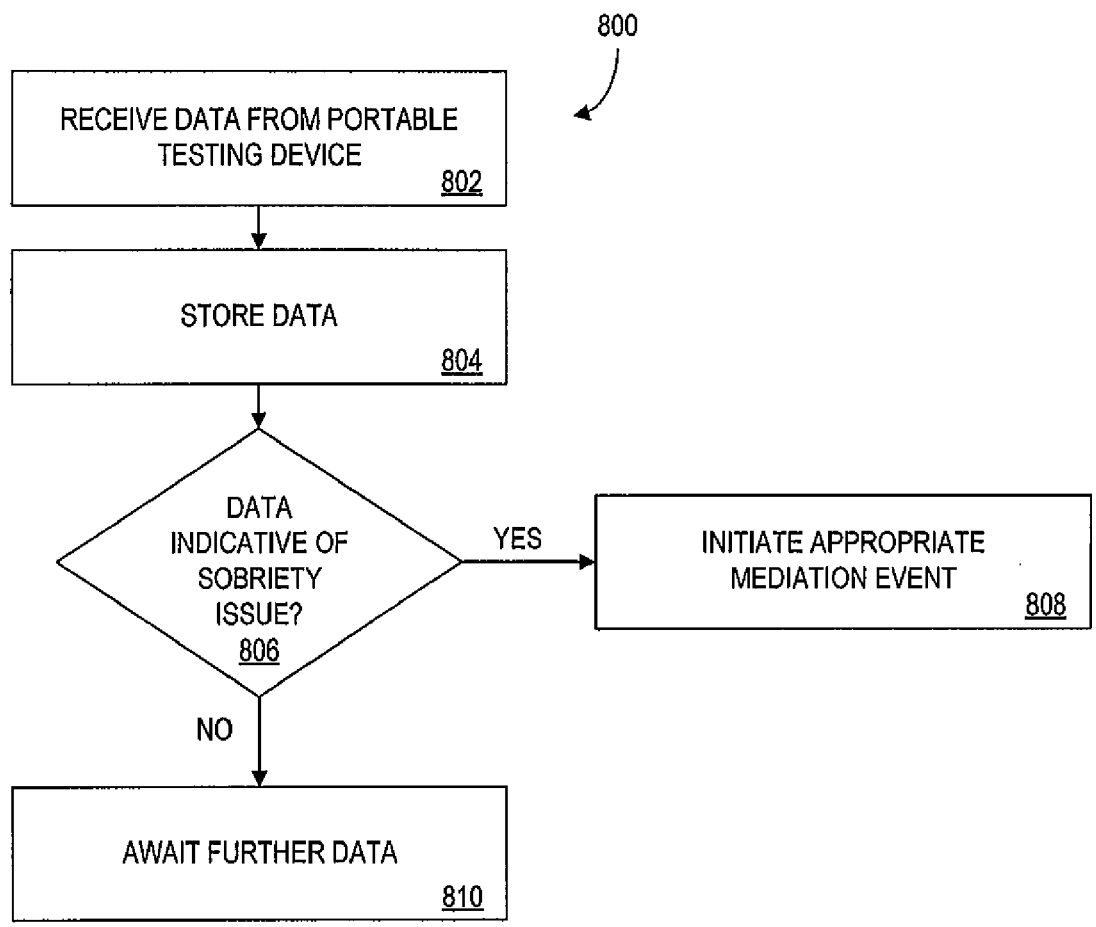
FIG. 8 is a flowchart illustrating a method according to one or more embodiments described herein.

Turning now to FIG. 8, a flow diagram of a method 800 according to some embodiments is shown. The method 800 may, for example, be performed by or on behalf of an operator of a sobriety testing service. For purposes of brevity, the method 800 will be described herein as being performed by a server computer 102 (e.g., a server computer operated by an online casino). However, in other embodiments some or all of the steps may be performed by another device (e.g., a portable testing device 108 and/or a remote gaming computer 106). It should further be noted that while all of the steps described with respect to method 800 may be performed by a single device, in some embodiments different steps may be performed by different devices. Further any steps described herein as being performed by a particular computing device may be performed by a human or another computing device as appropriate.

According to some embodiments, the method 800 may comprise receiving data from a portable testing device (step 802). For example, a portable testing device may be programmed to automatically (or at the direction of the player or a remote server computer) transmit data such as data related to the wagering activity of a player participating in an online gambling session (e.g., whether the player is participating in an online gambling session, the game the player is playing, a magnitude of wager(s) the player is placing, a frequency with which a player is placing wagers, losses incurred by the player, etc.) and/or data related to a sobriety test (e.g., raw data or a score comprising a result of a sobriety test administered to the player). Such a transmission may occur on a periodic or non-periodic bases. For example, such data may be transmitted upon being obtained by the portable testing device, at some periodic intervals, or upon request.

In step 804, the data received from the portable testing device is stored (e.g., temporarily), for subsequent use. For example, a result of a sobriety test may be stored for purposes of assessing a pattern in the results of sobriety tests taken by a particular player.

In step 806 it is determined whether the data received in step 802 is indicative of a sobriety issue (e.g., does the data indicate that the player is unacceptably intoxicated). If it is determined that the player is unacceptably intoxicated, an appropriate mediation even is initiated in step 808. Otherwise, the receipt of further data is awaited in step 810. For example, the results of a subsequent sobriety score may be awaited or further wagering activity data may be awaited (e.g., to determine whether the player is intoxicated or to determine whether a condition for administering a sobriety test has been satisfied).

Figure 9:
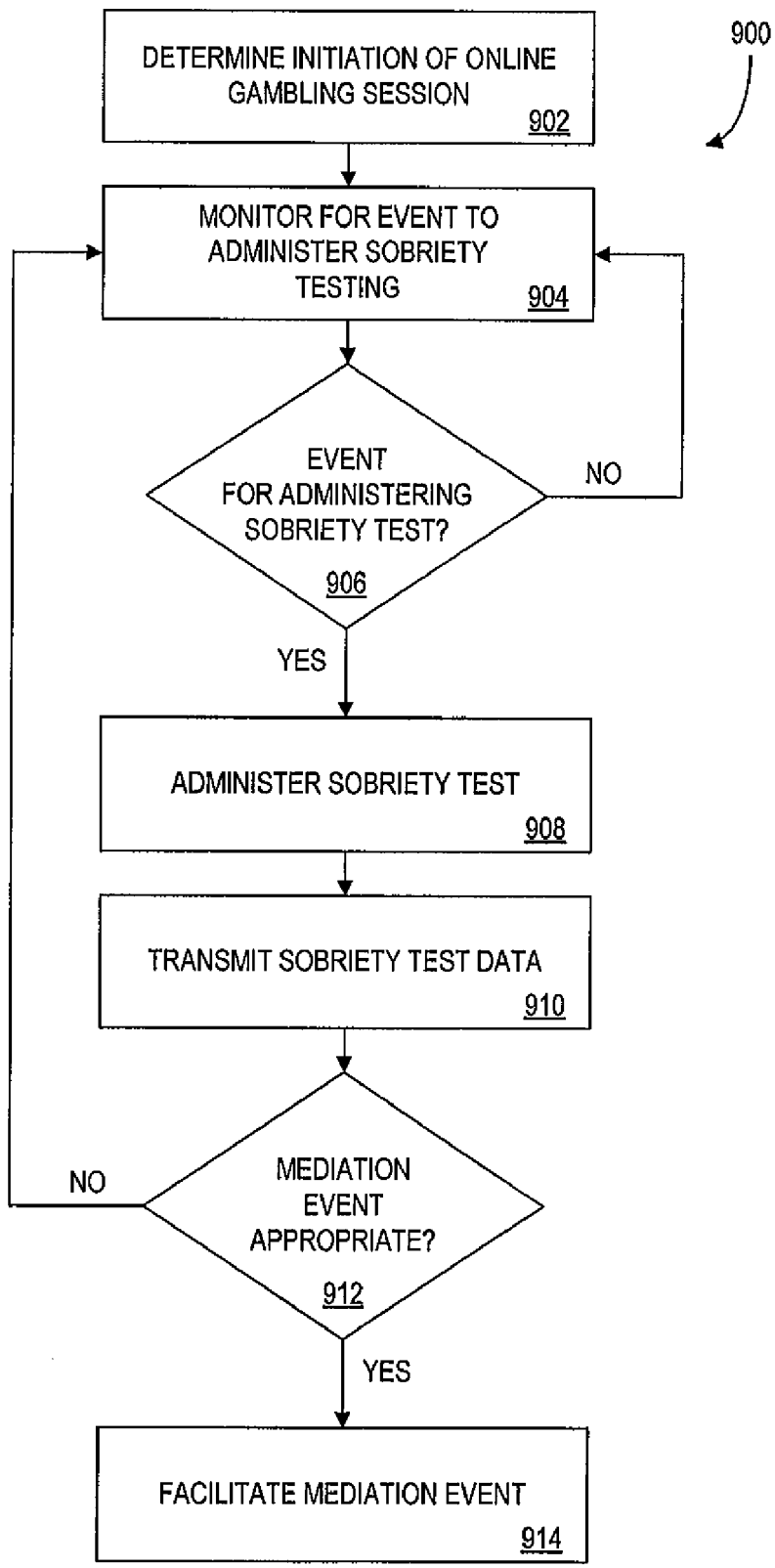
FIG. 9 is a flowchart illustrating a method according to one or more embodiments described herein.

Turning now to FIG. 9, a flow diagram of a method 900 according to some embodiments is shown. The method 900 may, for example, be performed by or on behalf of an operator of a sobriety testing service. For purposes of brevity, the method 900 will be described herein as being performed by a server computer 102 (e.g., a server computer operated by an online casino). However, in other embodiments some or all of the steps may be performed by another device (e.g., a portable testing device 108 and/or a remote gaming computer 106). It should further be noted that while all of the steps described with respect to method 900 may be performed by a single device, in some embodiments different steps may be performed by different devices. Further any steps described herein as being performed by a particular computing device may be performed by a human or another computing device as appropriate.

According to some embodiments, the method 900 may comprise determining an initiation of an online gambling session (step 902). This step may be similar to that described with respect to step 602 (FIG. 6). In step 904, monitoring for an event which may trigger the administration of a sobriety test is performed. Such an event may comprise, for example, monitoring for a particular time and/or data related to wagering activity of a player.

Various different factors may be useful in determining whether, when and to whom to administer a sobriety test. The following are non-limiting examples of such factors:

(i) Players may be given a sobriety test at the beginning of a gambling session. In one example, players may be required to complete a sobriety test at the beginning of every session. In another example, players may be required to complete a sobriety test at the beginning of specific sessions, such as the beginning of every other session, the beginning of every five sessions, the beginning of sessions that are initiated within a certain time frame (e.g., between 5 pm and 8 am), etc.

(ii) Players may be given a sobriety test between games in the middle of a gaming session—in between hands of blackjack as an example. Herein, a "game" can be interpreted to broadly refer to one instance of a wagering game, such as but not limited to the completion of the following gaming events: the placement of one or more wagers by one or more players, the revelation of one or more outcomes, and any payouts resulting from the one or more outcomes. In one example, a player may be given a sobriety test after he or she receives an outcome for a game (e.g., a spin of the slot reels). In another example, a player may be given a sobriety test right after requesting the start of a new game (e.g., a new hand of blackjack).

(iii) Players may be given a sobriety test in the middle of a game—in between gaming events for example. For example, a player may be given a sobriety test after placement of wager but before the revelation of the outcome. Providing sobriety tests in this fashion has the added benefit of creating motivation for the player to complete the test—players are anticipating the outcome, and will want to finish the test so that they can see whether or not they won.

Various criteria may be used to determine how often, in accordance with some embodiments, a player may be required to take a sobriety test. In some embodiments a player may be required to take a sobriety test periodically (e.g., periodically within a gambling session). For example, players may be required to take at least one sobriety test for every x units of time. In another example, players may be required to complete a sobriety test in each of every 30 minutes spent playing a wagering game. In yet another examples, players may be required to complete one or more sobriety tests for every 2 hours day, week, year, etc. In some embodiments, players may be provided with a sobriety tests at random intervals. For example a random number generator may be used to schedule when players are to receive a sobriety test. In some embodiments, the time of day or the calendar date may affect the frequency of sobriety tests. For example, a sobriety testing system may require more frequent testing at night or on weekends because players are more likely to be consuming alcohol or taking drugs at those times.

Various criteria may be used to identify which player(s) to test. The following are example criteria that may be used to determine how players may be selected to receive sobriety tests, as well as some examples of how frequently they receive them. In other words, the following may be rules used when determining if and when a player should receive a sobriety test.

(i) All players may receive tests in the same manner. In some embodiments, all players are provided with sobriety tests and with the same frequency. The criteria above may determine how often a player receives a test.

(ii) Players may receive a test based on one or more game data or events, such as, but not limited to rate of play, size of wagers, one or more consecutive losses, wins or outcomes, etc. For example, if a player loses a threshold amount of money, if a player loses a threshold amount of money within a specific period of time, if a player is playing very slowly, if a player is playing very quickly, if a player places a wager more than a threshold amount are all examples of data that may be useful in determining whether to administer a sobriety test to a particular player.

(iii) Players may receive sobriety tests based on a variety of personal information that they have provided to an online casino. For example, a player who is 25 may receive a test more frequently than a 60 year old player. In another example, males may receive more frequent testing than females.

(iv) A test may be provided to a player based on the results of a prior test. For example, if a player has recently failed a test in a previous gaming session, then that player may be given tests more frequently. In another example, if a player passed a previous test, but performed poorly, then a player may be given more frequent testing. This is particularly important because such a player may be drinking and pass a test, but then shortly thereafter the effects of the alcohol may kick in and put the player over the limit.

(v) A player may be given a test as a result of the player (or another entity) selecting an option to receive sobriety tests. For example, players may be asked if they want to participate in sobriety tests when beginning a session or when registering with an online casino. Additionally, testing requested by another person, such as a friend or family member. For example, if a player has a drinking problem, his parents may register him in a program that provides sobriety tests while gambling.

Returning now to FIG. 9, it is determined in step 906 whether an event has occurred which triggers the need to administer a sobriety test to an online gambler. Such a determination may be made based on any of the factors described above, and other factors which may become apparent upon a reading of the present disclosure. If it is determined that a sobriety test is to be administered, the process moves to step 908. Otherwise, the process returns to the monitoring step 904.

In step 908, a sobriety test is administered. A wide variety of types of sobriety tests are described herein. In step 910, the sobriety test data may be transmitted. For example, if a sobriety test is administered by a remote gaming computer 106 and/or a portable testing device 108, data related to the sobriety test (e.g., raw data, a score, etc.) may be transmitted to a sobriety testing system 110.

In step 912 it is determined whether a mediation event is appropriate, based on the sobriety test data. A wide variety of factors which may be used to determine whether to initiate a mediation event are described herein. In some embodiments, step 912 may comprise determining which mediation event or events to initiate. In step 914, the mediation event is facilitated if it is determined that one is appropriate. For example, instructions or information may be output to a player, a player's portable testing device and/or a remote gaming computer. In another example, a player's wagering activity may be paused or interrupted by an online casino (e.g., based on a notification or instructions received from a sobriety testing system, a remote gaming computer and/or a portable gaming device). If a mediation event is not appropriate, the process 900 returns to the monitoring step 904.

F. Interpretation

Numerous embodiments are described in this disclosure, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this disclosure) nor the Abstract (set forth at the end of this disclosure) is to be taken as limiting in any way as the scope of the disclosed invention(s).

The term "product" means any machine, manufacture and/or composition of matter as contemplated by 35 U.S.C. §101, unless expressly specified otherwise.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "plurality" means "two or more", unless expressly specified otherwise.

The term "herein" means "in the present disclosure, including anything which may be incorporated by reference", unless expressly specified otherwise.

The phrase "at least one of", when such phrase modifies a plurality of things (such as an enumerated list of things) means any combination of one or more of those things, unless expressly specified otherwise. For example, the phrase at least one of a widget, a car and a wheel means either (i) a widget, (ii) a car, (iii) a wheel, (iv) a widget and a car, (v) a widget and a wheel, (vi) a car and a wheel, or (vii) a widget, a car and a wheel.

The phrase "based on" does not mean "based only on", unless expressly specified otherwise. In other words, the phrase "based on" describes both "based only on" and "based at least on".

Where a limitation of a first claim would cover one of a feature as well as more than one of a feature (e.g., a limitation such as "at least one widget" covers one widget as well as more than one widget), and where in a second claim that depends on the first claim, the second claim uses a definite article "the" to refer to the limitation (e.g., "the widget"), this does not imply that the first claim covers only one of the feature, and this does not imply that the second claim covers only one of the feature (e.g., "the widget" can cover both one widget and more than one widget).

Each process (whether called a method, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device or article is described herein, more than one device or article (whether or not they cooperate) may alternatively be used in place of the single device or article that is described. Accordingly, the functionality that is described as being possessed by a device may alternatively be possessed by more than one device or article (whether or not they cooperate).

Similarly, where more than one device or article is described herein (whether or not they cooperate), a single device or article may alternatively be used in place of the more than one device or article that is described. For example, a plurality of computer-based devices may be substituted with a single computer-based device. Accordingly, the various functionality that is described as being possessed by more than one device or article may alternatively be possessed by a single device or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display. The aspect ratio of the display may be 4:3, 16:9, or the like. Furthermore, the resolution of the display may be any appropriate resolution such as 480i, 480p, 720p, 1080i, 1080p or the like. The format of information sent to the display may be any appropriate format such as Standard Definition Television (SDTV), Enhanced Definition TV (EDTV), High Definition TV (HDTV), or the like. The information may likewise be static, in which case, painted glass may be used to form the display. Note that static information may be presented on a display capable of displaying dynamic information if desired. Some displays may be interactive and may include touch screen features or associated keypads as is well understood.

The present disclosure may refer to a "control system". A control system, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dongle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" is an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate via such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

What is claimed is:

1. A method for operating a sobriety testing service for online gamblers, comprising:
   receiving, at a computing device, an indication of an online gambler initiating a gambling session;
   determining, by the computing device, to administer a sobriety test to the online gambler;
   facilitating the administration of the sobriety test to the online gambler;
   determining that a result of the sobriety test indicates the player is unacceptably intoxicated; and facilitating a mediation event responsive to the determination of the result.

2. The method of claim 1, wherein the method further comprises providing a wagering game over a network to the online gambler.

3. The method of claim 1 being performed by a portable testing device operatively connected to a computing device being used by the online gambler for engaging in a wagering game over the network, the method further comprising transmitting, over a network, the result of the sobriety test to a remote computer distinct from the computing device being used by the player.

4. The method of claim 3, wherein facilitating the mediation event comprises initiating the mediation event from the portable testing device.

5. The method of claim 4, wherein initiating the mediation event comprises directing the computing device being used by the online gambler to perform a function that intervenes in the player's wagering activity.

6. The method of claim 3, wherein facilitating the mediation event comprises receiving an instruction from the remote computer, the instruction including an indication of the mediation event.

7. The method of claim 1, wherein facilitating the sobriety test comprises administering the sobriety test to the online gambler.

8. The method of claim 7, wherein administering the sobriety test comprises administering the sobriety test over the network, wherein a computer program comprising the sobriety test resides on a remote computing device in communication with a computer being used by the player to engage in wagering activity.

9. The method of claim 7, wherein the sobriety test comprises a verbal test in which the player speaks words into a microphone of a computing device, for analysis of the player's intoxication.

10. The method of claim 7, wherein the sobriety test comprises questions that the player answers, for analysis of the player's intoxication.

11. The method of claim 7, wherein the sobriety test comprises a dexterity test in which the player tracks with a mouse pointing device of a computer an object on a computer screen of the computer.

12. The method of claim 7, wherein the sobriety test comprises a dexterity test in which the player uses a keyboard to type a predetermined set of alphanumeric symbols into a text field.

13. The method of claim 7, wherein the sobriety test comprises a task integrated into a wagering game engaged in by the player.

14. The method of claim 7, wherein facilitating the administration of the sobriety test comprises facilitating the administration of the sobriety test to the player in a manner that is transparent to the player, such that it appears to the player that the player is continuing to engage in a wagering activity and not participating in a sobriety test.

15. The method of claim 7, wherein facilitating the administration of the sobriety test comprises facilitating a pausing of a wagering activity being engaged in by the player in order to have the sobriety test administered to the player.

16. The method of claim 1, wherein determining to administer a sobriety test comprises determining that a predetermined event for triggering the administration of the sobriety test has occurred.

17. The method of claim 16, wherein the predetermined event comprises a predetermined time, a predetermined period of time since a previous administration of a sobriety test to the online gambler, a random selection of the player, an instruction being received to administer the sobriety test and an act performed by the player while engaged in a wagering activity.

18. The method of claim 1, wherein determining that a result of the sobriety test indicates the player is unacceptably intoxicated comprises comparing the result of the sobriety test to a result of a previously administered sobriety test.

19. The method of claim 18, wherein the result of the previously administered sobriety test comprises a baseline result of a sobriety test administered to the player at a time the player was believed to not be intoxicated.

20. The method of claim 1, wherein determining to administer a sobriety test comprises determining that a state of a characteristic of the player's current wagering activity is a deviation from a state of the characteristic in the player's past wagering activity.

21. The method of claim 1, further comprising: alerting a third party as to the result of the sobriety test.

22. The method of claim 1, wherein determining, by the computing device, to administer a sobriety test to the online gambler comprises determining an aspect of a current gambling session.

23. The method of claim 21, wherein an aspect of a current gambling session may comprise one or more of (i) an amount lost, (ii) a rate at which wagers are placed, (iii) the session length (iv), average wager size, (v) a previous sobriety test, (vi) the results of a previous sobriety test, (vii) a player's profile, and (viii) a date and time.

24. The method of claim 1, wherein determining, by the computing device, to administer a sobriety test to the online gambler comprises one or more of (i) a determination a type of sobriety test to be administered and (ii) a determination of a difficulty of the sobriety test.

25. An apparatus for facilitating the operation of a sobriety testing service for online gamblers, comprising:
a processor;
a memory, the memory storing a program for directing the processor, the processor being operable with the program to perform a method comprising:
receiving an indication of an online gambler initiating a gambling session over a network;
determining by the computing device, to administer a sobriety test to the online gambler;
facilitating the administration of the sobriety test to the online gambler;
determining that a result of the sobriety test indicates the player is unacceptably intoxicated; and
facilitating a mediation event responsive to the determination of the result.

26. A computer-readable medium storing instructions for directing a processor, the instructions causing the processor to perform a method comprising:
receiving an indication of an online gambler initiating a gambling session over a network;
determining, by the computing device, to administer a sobriety test to the online gambler;
facilitating the administration of the sobriety test to the online gambler;
determining that a result of the sobriety test indicates the player is unacceptably intoxicated; and
facilitating a mediation event responsive to the determination of the result.

* * * * *